(12) United States Patent
Ehlert et al.

(10) Patent No.: US 11,185,260 B1
(45) Date of Patent: Nov. 30, 2021

(54) STATE-BASED METHODS AND SYSTEMS USING CONTINUOUS GLUCOSE MONITORS AND ACCELEROMETERS TO REGULATE GLUCOSE LEVELS

(71) Applicant: Optum Labs, LLC, Minnetonka, MN (US)

(72) Inventors: Kenneth S Ehlert, Brooklyn Park, MN (US); Steven Catani, Athens, GA (US); Shane Hoversten, Brooklyn Park, MN (US); Grant Brian Weller, Nashville, TN (US)

(73) Assignee: Optum Labs, LLC, Minnetonka, MN (US)

( * ) Notice: Subject to any disclaimer, the term of this patent is extended or adjusted under 35 U.S.C. 154(b) by 490 days.

(21) Appl. No.: 16/103,567

(22) Filed: Aug. 14, 2018

(51) Int. Cl.
*A61B 5/00* (2006.01)
*A61B 5/145* (2006.01)
(Continued)

(52) U.S. Cl.
CPC ........ *A61B 5/14532* (2013.01); *A61B 5/0022* (2013.01); *A61B 5/02055* (2013.01); *A61B 5/1118* (2013.01); *A61B 5/681* (2013.01); *A61B 5/6824* (2013.01); *G16H 20/10* (2018.01); *G16H 20/60* (2018.01); *G16H 50/20* (2018.01);
(Continued)

(58) Field of Classification Search
CPC . A61B 5/14532; A61B 5/1118; A61B 5/0022; A61B 5/6824; A61B 5/681; A61B 5/02055; A61B 5/7267; A61B 5/0531; A61B 5/4866; A61B 5/01; A61B 2562/0219; A61B 5/7275; A61B 5/02405;
(Continued)

(56) References Cited

U.S. PATENT DOCUMENTS

| 5,398,688 A | 3/1995 | Laniado |
| 6,508,762 B2 | 1/2003 | Karnieli |

(Continued)

OTHER PUBLICATIONS

United States Patent and Trademark Office, NonFinal Office Action for U.S. Appl. No. 15/971,835, filed Jun. 5, 2020, (26 pages), USA.
(Continued)

*Primary Examiner* — Andrey Shostak
(74) *Attorney, Agent, or Firm* — Alston & Bird LLP

(57) ABSTRACT

Embodiments include methods and systems for regulating a user's glucose levels. Systems comprise a processing unit in communication with a glucose monitor, an accelerometer, and a user interface. The glucose monitor generates glucose readings corresponding to the user's glucose levels and the accelerometer generates acceleration readings corresponding to the user's activity. The processing unit determines if the glucose readings indicate a glucose state and whether the acceleration readings indicate an activity state. If the glucose state and the activity state coincide, the processing unit sends a message to the user interface recommending a behavior that would influence the user's glucose level. Methods comprise determining, at a processing unit, if glucose readings indicate a glucose state, if acceleration readings indicate an activity state, whether the glucose state and activity state coincide and, if so, sending a message to a user interface recommending a behavior that would influence the user's glucose level.

4 Claims, 16 Drawing Sheets

(51) Int. Cl.
*A61B 5/0205* (2006.01)
*G16H 50/20* (2018.01)
*G16H 20/10* (2018.01)
*A61B 5/11* (2006.01)
*G16H 20/60* (2018.01)
*A61B 5/0531* (2021.01)
*A61B 5/01* (2006.01)
*A61B 5/024* (2006.01)
*G16H 10/60* (2018.01)
*G16H 50/50* (2018.01)

(52) U.S. Cl.
CPC ............. *A61B 5/01* (2013.01); *A61B 5/02405* (2013.01); *A61B 5/0531* (2013.01); *A61B 5/4866* (2013.01); *A61B 5/7267* (2013.01); *A61B 5/7275* (2013.01); *A61B 2562/0219* (2013.01); *G16H 10/60* (2018.01); *G16H 50/50* (2018.01)

(58) Field of Classification Search
CPC ........ G16H 20/60; G16H 20/10; G16H 50/20; G16H 50/50; G16H 10/60
See application file for complete search history.

(56) References Cited

U.S. PATENT DOCUMENTS

| | | | |
|---|---|---|---|
| 6,735,477 B2 | 5/2004 | Levine | |
| 8,568,309 B2 | 10/2013 | Angelides | |
| 8,803,688 B2 | 8/2014 | Halff | |
| 8,870,766 B2 | 10/2014 | Stivoric et al. | |
| 9,168,000 B2 | 10/2015 | Dunki-Jacobs et al. | |
| 9,685,097 B2 | 6/2017 | Hoover et al. | |
| 9,955,914 B2 | 5/2018 | Dunki-Jacobs et al. | |
| 10,130,277 B2 | 11/2018 | Connor | |
| 10,314,492 B2 | 6/2019 | Connor | |
| 10,446,054 B2 | 10/2019 | Lamoncha | |
| 2002/0167863 A1 | 11/2002 | Davis et al. | |
| 2008/0262745 A1 | 10/2008 | Polidori | |
| 2009/0177068 A1 | 7/2009 | Stivoric et al. | |
| 2010/0324432 A1 | 12/2010 | Bjoerling et al. | |
| 2010/0331657 A1 | 12/2010 | Mensinger et al. | |
| 2011/0021898 A1 | 1/2011 | Wei et al. | |
| 2011/0270052 A1* | 11/2011 | Jensen | A61B 5/0002 600/302 |
| 2012/0059237 A1 | 3/2012 | Amir et al. | |
| 2013/0211220 A1 | 8/2013 | Cobelli et al. | |
| 2014/0005499 A1* | 1/2014 | Catt | A61B 5/7246 600/301 |
| 2015/0045238 A1 | 2/2015 | Chan et al. | |
| 2015/0217052 A1 | 8/2015 | Keenan et al. | |
| 2015/0317913 A1* | 11/2015 | Angelides | A61B 5/74 434/127 |
| 2017/0049332 A1 | 2/2017 | Park et al. | |
| 2017/0164878 A1 | 6/2017 | Connor | |
| 2017/0249445 A1 | 8/2017 | Devries et al. | |
| 2018/0277246 A1 | 9/2018 | Zhong et al. | |
| 2019/0167190 A1 | 6/2019 | Choi et al. | |
| 2019/0209022 A1 | 7/2019 | Sobol et al. | |
| 2019/0252079 A1* | 8/2019 | Constantin | A61B 5/14532 |

OTHER PUBLICATIONS

U.S Patent and Trademark Office, NonFinal Office Action for U.S. Appl. No. 15/372,005, filed Oct. 9, 2019, (26 pages), USA.

Final Office Action for U.S. Appl. No. 15/971,835, filed Nov. 16, 2020, (13 pages), United States Patent and Trademark Office, U.S.

Bruno, Barbara et al. "Analysis of Human Behavior Recognition Algorithms Based On Acceleration Data," 2013 IEEE International Conference on Robotics and Automation (ICRA), pp. 1602-1607, (2013).

Bruno, Barbara et al. "Human Motion Modelling and Recognition: A Computational Approach," Eighth IEEE International Conference on Automation Science and Engineering (CASE), Aug. 20-24, 2012, pp. 156-161 (2012), Seoul Korea.

Chevalier, Guillame. "LSTMs for Human Activity Recognition," (2016), (14 pages). [Retrieved from the Internet Aug. 22, 2019] <https://github.com/guillaume-chevalier/LSTM-Human-Activity-Recognition>.

Monte-Moreno, Enric. "Non-Invasive Estimate of Blood Glucose and Blood Pressure From A Photoplethysmograph By Means of Machine Learning Techniques," Artificial Intelligence in Medicine, 53(2), (2011), pp. 127-138.

Schianca, Gian Piero Carnevale et al., "The Significance of Impaired Fasting Glucose Versus Impaired Glucose Tolerance," Diabetes Care, vol. 26, No. 5, May 2003, pp. 1333-1337, American Diabetes Association.

Thomaz, Edison et al. "A Practical Approach For Recognizing Eating Moments With Wrist-Mounted Inertial Sensing," Proceedings of the 2015 ACM International Joint Conference on Pervasive and Ubiquitous Computing (UbiComp '15) ACM, New York, NY, USA, pp. 1029-1040 (2015). [Retrieved from the Internet Aug. 22, 2019] <https://doi.org/10.1145/2750858.2807545>.

Wikipedia, "Insulin Resistance," Dec. 7, 2016, (17 pages) [Retrieved from the Internet Aug. 22, 2019] <https://en.wikipedia.org/wiki/Insulin_resistance#Fasting_insulin_levels>.

Notice of Allowance and Fee(s) Due for U.S. Appl. No. 15/971,835, filed Mar. 18, 2021, (9 pages), United States Patent and Trademark Office, US.

* cited by examiner

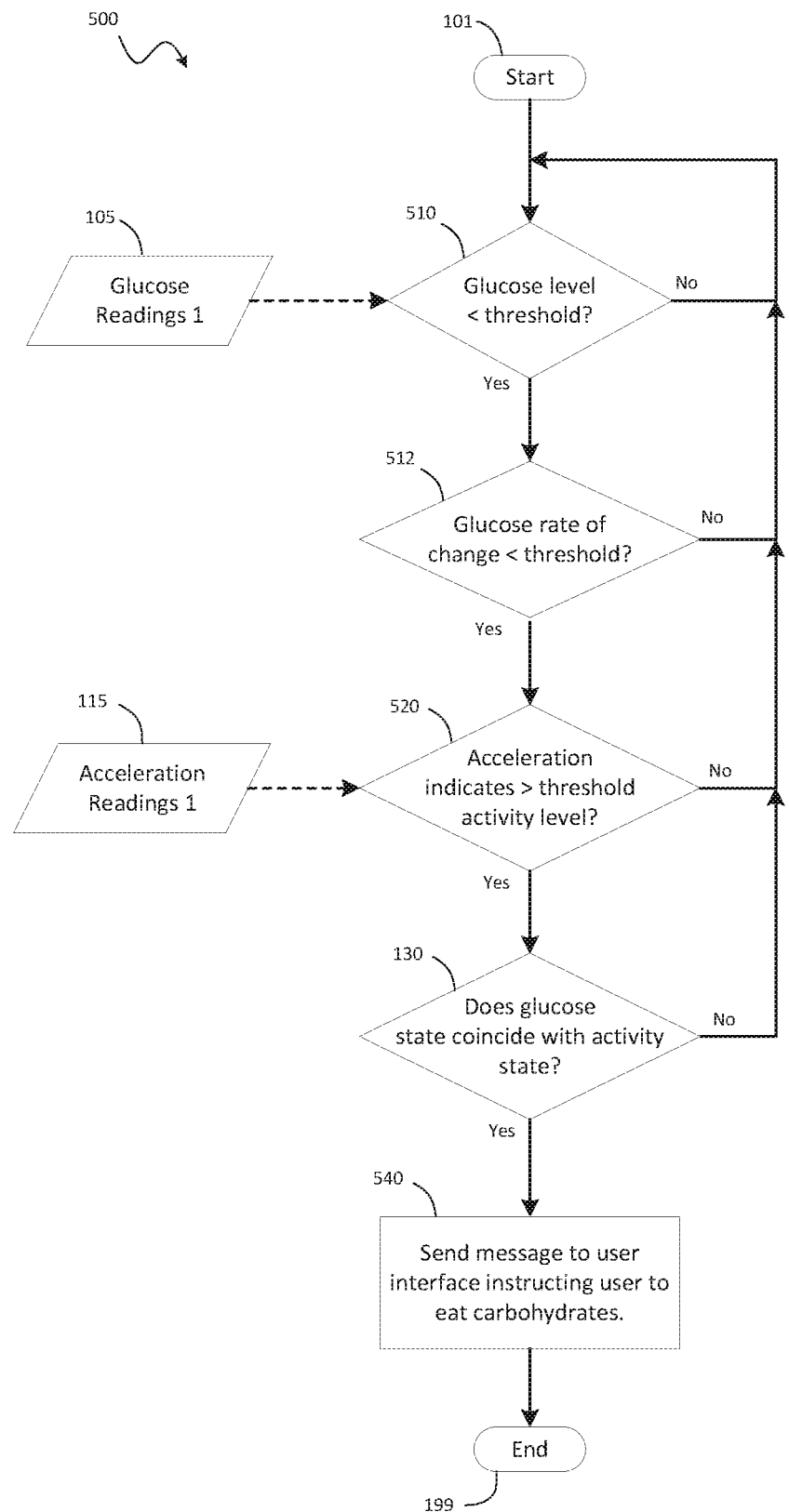

STATE-BASED METHODS AND SYSTEMS USING CONTINUOUS GLUCOSE MONITORS AND ACCELEROMETERS TO REGULATE GLUCOSE LEVELS

TECHNICAL FIELD

Embodiments relate to systems and methods for regulating bodily glucose levels with continuous glucose monitors and accelerometers.

BACKGROUND

Glucose levels in the body have profound effects on health. When glucose levels go above or below optimal levels, serious health problems may result. If glucose levels are too low, a person may become unconscious or, in extreme cases, even die. If glucose levels become too high, vascular damage and blindness may result. Even in less extreme situations, glucose levels above or below an optimal range may cause or exacerbate a host of health conditions.

When bodily systems regulating glucose are functioning properly, glucose levels remain in a healthy range through processes including glucose disposal, glycogen breakdown, and gluconeogenesis. Glucose levels may be regulated by a number of hormones including insulin. Two causes of glucose dysregulation relate to insulin. First, pancreatic beta cells may partially or completely lose their ability to produce insulin. This cause of dysregulation may be referred to as impaired beta cell capacity (BCC). Second, cells in the body that increase their uptake of glucose in response to insulin may partially or completely lose their responsiveness to insulin. This second cause of dysregulation may be referred to as insulin resistance.

While the regulation of glucose is a complex physiological process, there are a limited number of behavioral factors that can influence glucose levels. Eating may increase glucose levels. Physical activity may cause cells to metabolize glucose more quickly and thus decrease glucose levels below what they would otherwise be. Notably, physical activity may reduce glucose levels without involving insulin and thus provide a useful tool for regulating glucose levels of those with insulin resistance or impaired BCC. A variety of medications, including insulin, can also influence glucose levels. Sleep patterns may affect glucose levels as well.

Maintaining glucose levels within a healthy range remains challenging for many people. Reasons for the difficulty include metabolic variability among individuals. Individuals respond differently to food intake, physical activity, medications, stress, and sleep. As a result, generalized advice to diabetics is often ineffective in controlling their glucose levels. A common challenge to maintaining healthy glucose levels involves the rapid increase in glucose levels (sometimes referred to as "spikes") that occur after eating. People with insulin resistance may have difficulty maintaining their post-prandial glucose levels. Properly timed post-meal exercise and pre-meal medication may reduce post-prandial glucose spikes. Physical activity, in particular, can reduce glucose spikes in insulin-resistant people. However, determining optimal times and quantities of physical activity and medication relative to eating remains challenging. This is due in part to individual variation. Anticipating hyperglycemia and hypoglycemia and informing individuals of the need for glucose-influencing behaviors before such behaviors are needed remains challenging as well.

SUMMARY

Embodiments include systems and methods for regulating a user's glucose levels. Systems comprise a processing unit in communication with a glucose monitor, an accelerometer, and a user interface. The glucose monitor generates glucose readings corresponding to the user's glucose levels and the accelerometer generates acceleration readings corresponding to the user's activity. The processing unit determines if a set of the glucose readings satisfies one or more glucose criteria, thereby indicating that the user is in a glucose state. The processing unit determines if a set of the acceleration readings satisfies one or more acceleration criteria indicating that the user is in an activity state. The processing unit then determines whether the glucose state and activity state coincide (occur at the same time). If so, the processing unit sends a message to the user interface recommending a behavior that would influence the user's glucose level.

Methods comprise determining, at a processing unit, if a set of glucose readings satisfies one or more glucose criteria thereby indicating that a user is in a glucose state, determining whether a set of acceleration readings satisfies one or more acceleration criteria thereby indicating that the user in in an activity state, determining whether the glucose state and the activity state coincide and, if so, sending a message to a user interface recommending a behavior that would influence the user's glucose level.

BRIEF DESCRIPTION OF THE DRAWINGS

FIG. 5 presents a flowchart illustrating a method of regulating glucose levels using sensed data from a glucose monitor and an accelerometer to predict glucose deficiency, according to certain embodiments of the present disclosure.

DETAILED DESCRIPTION

Figure 1:
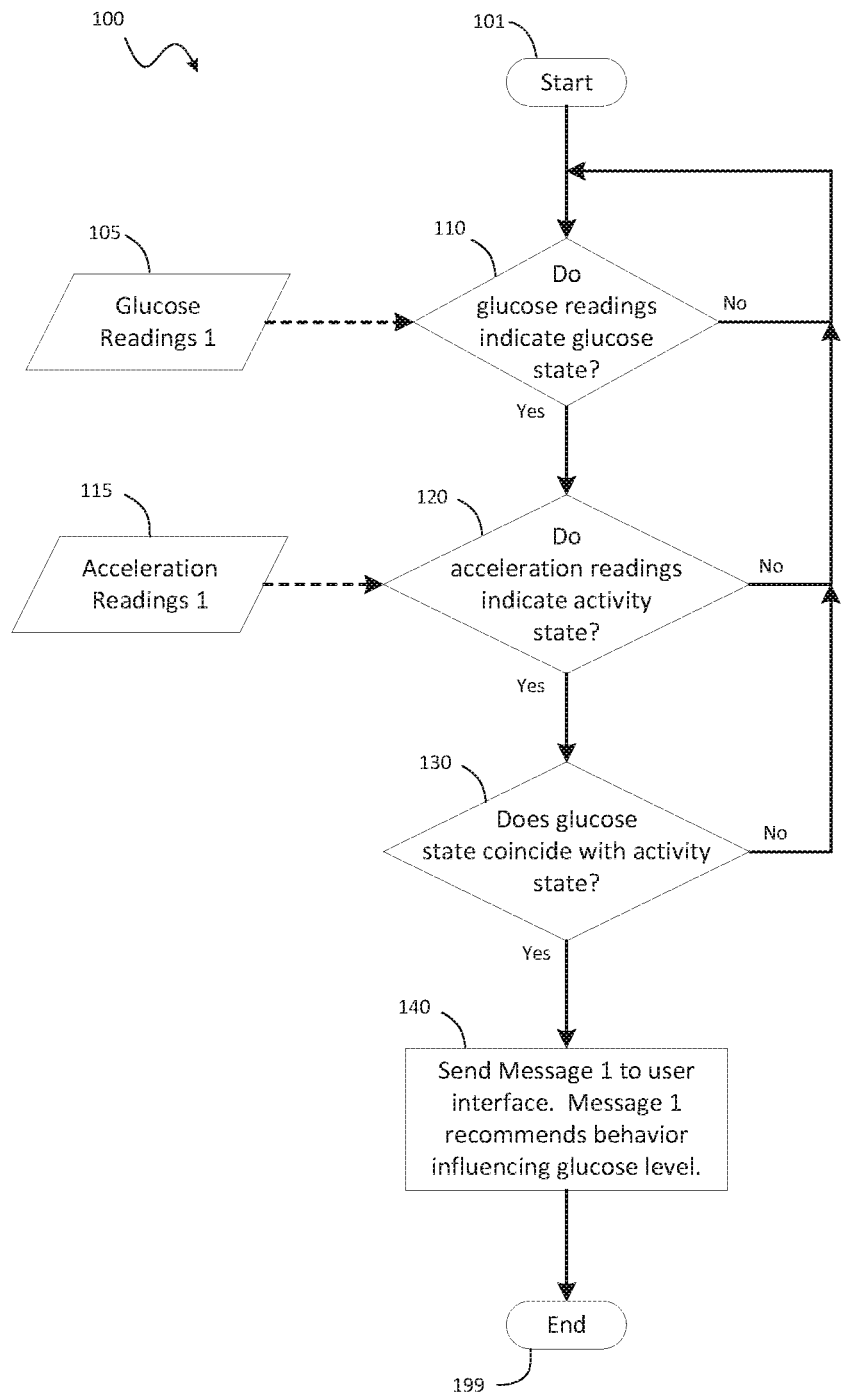
FIG. 1 presents a flowchart illustrating a method of regulating glucose levels using sensed data from a glucose monitor and an accelerometer, according to certain embodiments of the present disclosure.

Embodiments include methods and systems for regulating glucose levels of a user. Exemplary embodiments use glucose readings from a glucose monitor and acceleration readings from an accelerometer to select a message presented via a user interface. The message may advise the user to engage in or refrain from an activity, thereby influencing the user's glucose levels. The content and/or characteristics (including timing) of the message may be a function of the glucose readings and the acceleration readings. Messages may thereby be tailored to the needs of an individual to reinforce appropriately timed behaviors that maintain glucose levels within a healthy range. Embodiments may deliver these messages at or before the time at which the behavior is recommended.

Activities that may influence glucose levels include eating, physical activity, taking medications, sleeping, and relaxation techniques. Messages designed to address or prevent hyperglycemia may include those suggesting physical activity, refraining from eating sugars or other carbohydrates, taking anti-hyperglycemic medications including insulin, and practicing relaxation techniques. Messages to address hypoglycemia may suggest consuming sugars or other carbohydrates, refraining from physical activity, or decreasing dosage of anti-hyperglycemic drugs. Messaging promoting healthy sleep habits may be advisable under a variety of conditions and benefit glucose control.

Glucose levels in the body are often referred to as blood glucose levels because glucose levels in the blood may be an indicator of glucose levels throughout the body. However, glucose levels in other fluids and tissues may also be measured. As used herein, "blood glucose" may refer to bodily glucose levels unless otherwise indicated.

Method Embodiments

Embodiments of methods include receiving glucose readings at a processing unit. The glucose readings correspond to glucose levels of a user. The glucose readings may be analog, digital, or of another format and may or may not require conversion of the reading into a glucose level. The processing unit may then determine if the glucose readings, or any subset of them, satisfy one or more glucose criteria. Satisfying the one or more glucose criteria indicates that the user is in a glucose state. The user may remain in the glucose state so long as the glucose readings satisfy the one or more glucose criteria. Methods may also include receiving acceleration readings at the processing unit. The acceleration readings correspond to activity of the user. The acceleration readings may be analog, digital, or of another format and may or may not require conversion of the reading into a quantity of acceleration. The processing unit may then determine if the acceleration readings, or any subset of them, satisfy one or more acceleration criteria. Satisfying the one or more acceleration criteria indicates that the user is in an activity state. The user may remain in the activity state so long as the acceleration readings satisfy the one or more acceleration criteria. If the processing unit determines that the glucose state coincides with (occurs, at least momentarily, at the same time as) the activity state, it may send a message to a user interface. The message may recommend performing or refraining from a behavior that could influence the user's glucose level. The message may, optionally, be sent within a critical amount of time of the later-occurring of the glucose state or the activity state. In other words, the processing unit may send a message to the user interface within the critical amount of time of the time at which the glucose state and the activity state first coincide. Sending the message within the critical amount of time may be advantageous in embodiments for which message timing is influential in determining the message's effectiveness.

FIG. 1 presents a flowchart illustrating a method (100) of regulating glucose levels using sensed data from a glucose monitor and an accelerometer, according to certain embodiments of the present disclosure. After the start (101), a processing unit receives glucose readings (105). The processing unit then determines whether the glucose readings (105) indicate that the user is in a glucose state. (110) If not, processing repeats step 110 until the processing unit detects the glucose state. If the glucose state is detected, the processing unit then determines whether acceleration readings (115) it receives indicate that the user is in an activity state. (120) If not, processing returns to step 110 to determine whether glucose readings indicate the glucose state. If the activity state is detected, the processing unit then determines whether the activity state coincides with (occurs at the same time as) the glucose state. (130) If not, processing returns to step 110 until the glucose state is detected. If the glucose state and the activity state coincide, the processing unit sends a message to a user interface. (140) The message recommends performing or abstaining from an activity that affects the user's glucose level. After the processing unit sends the message to the user interface (140), the method (100) ends. (199)

Figure 2:
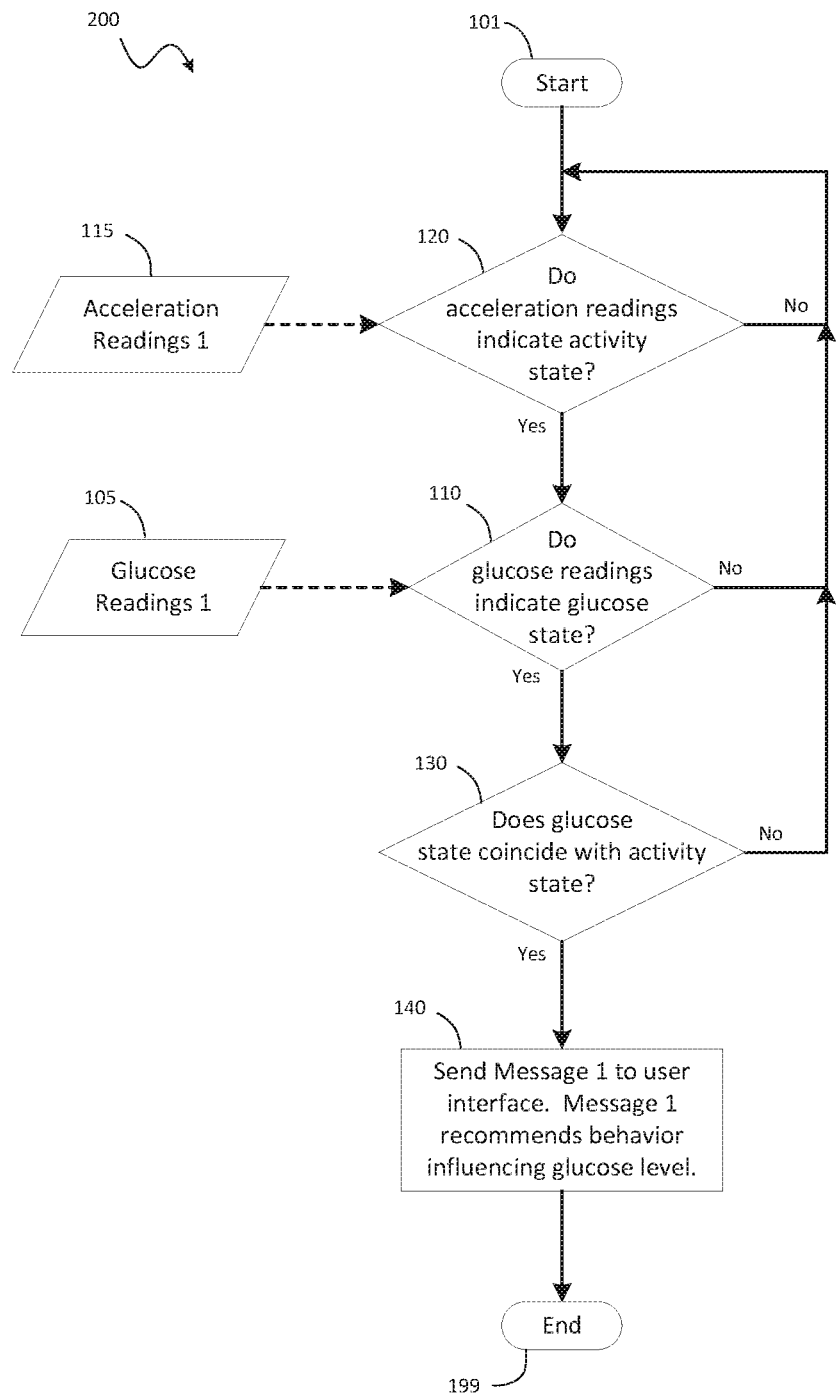
FIG. 2 presents a flowchart illustrating a method of regulating glucose levels using sensed data from an accelerometer and a glucose monitor, according to certain embodiments of the present disclosure.

Those with skill in the art will recognize that the order of detecting the glucose state and the activity state may be reversed so that glucose readings are only processed for recognition of a glucose state after the processing unit determines the presence of an activity state. This variation of the method is illustrated in FIG. 2. Alternatively, in processing units with multiple processors, the processing unit may simultaneously monitor glucose readings for the glucose state and monitor acceleration readings for the activity state and determine if the activity state coincides with the glucose state.

FIG. 2 presents a flowchart illustrating a method (200) of regulating glucose levels using sensed data from an accelerometer and a glucose monitor, according to certain embodiments of the present disclosure. After the start (101), a processing unit receives acceleration readings (115). The processing unit then determines whether the acceleration readings (115) indicate that the user is in an activity state. (120) If not, processing repeats step 120 until it detects the activity state. If the activity state is detected, the processing unit then determines whether glucose readings (105) indicate that the user is in a glucose state. (110) If not, processing returns to step 120 to determine whether acceleration readings indicate the activity state. If the glucose state is detected, the processing unit then determines whether the activity state coincides with the glucose state. (130) If not, processing returns to step 120 until the activity state is detected. If the glucose state and the activity state coincide, the processing unit sends a message to a user interface. (140) The message recommends performing or refraining from an activity that affects the user's glucose level. After the processing unit sends the message to the user interface (140), the method (200) ends. (199)

Elevated glucose levels before and during sleep may have deleterious effects on sleep quality. Poor sleep quality, in turn, may impede proper endocrine function, including the ability to regulate glucose levels. One embodiment of the method seeks to control elevated glucose levels before sleep onset. The user's bedtime may be inferred from time of day. Alternatively, customary bedtimes or may be entered by the user on a second user interface or times of sleep may be inferred from time periods with little or no acceleration activity on previous days and trends in sleep onset time may thereby be determined. Processors may have clocks that measure time by counting processing cycles and accordingly, determine the time at which a particular reading is received is feasible for most processing units. When glucose readings, or a derivative of glucose readings, exceed an optimal threshold within an amount of time before expected bedtime and acceleration readings indicate an activity level below an activity threshold (indicating decreased activity before sleep), the processing unit may send a message to the user interface suggesting that the user refrain from consuming glucose-elevating foods at that time.

Figure 3:
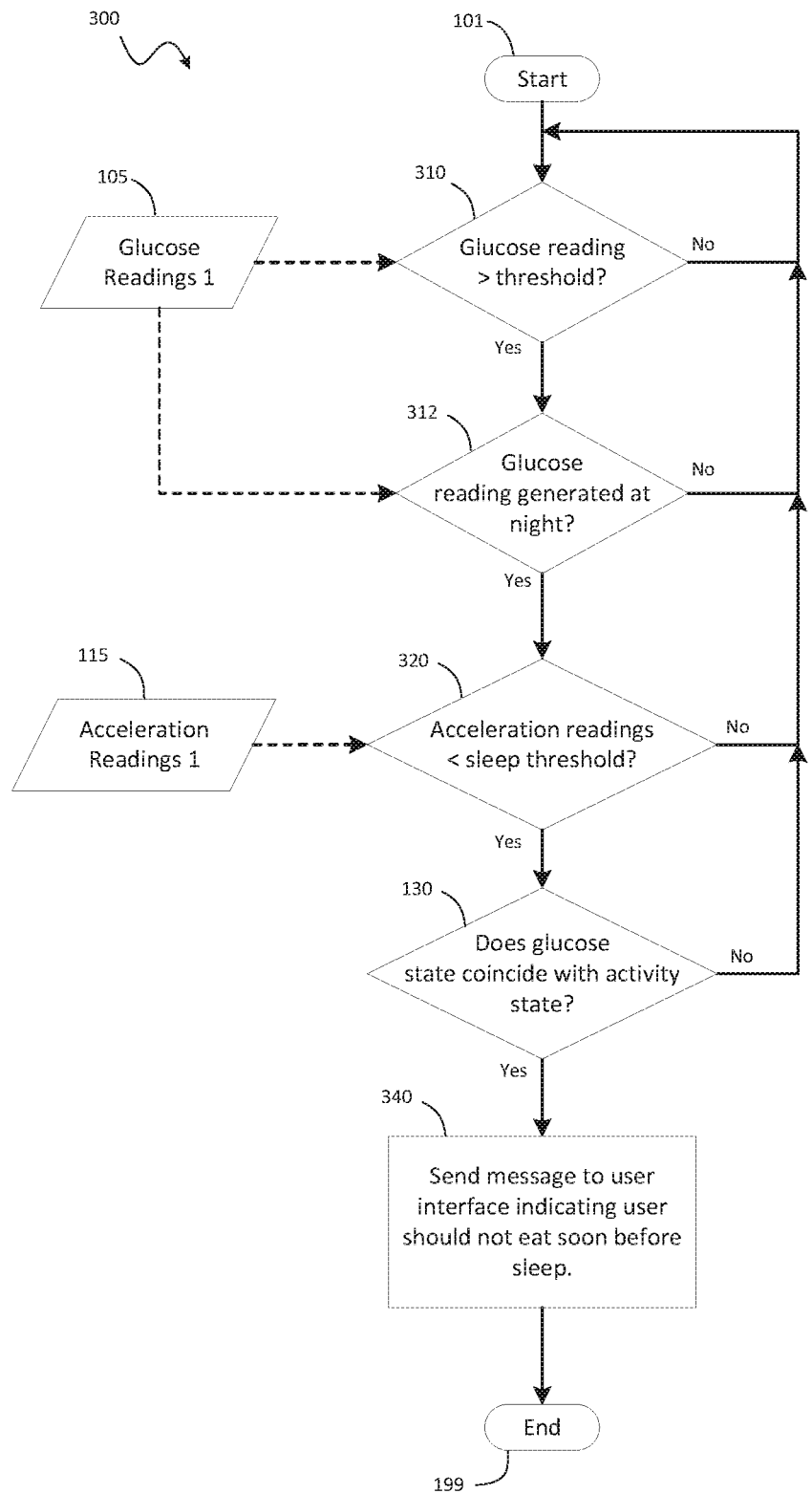
FIG. 3 presents a flowchart illustrating a method of regulating glucose levels using sensed data from a glucose monitor and an accelerometer to determine food consumption before sleep, according to certain embodiments of the present disclosure.

FIG. 3 presents a flowchart illustrating a method (300) of regulating glucose levels using sensed data from a glucose monitor and an accelerometer to determine food consumption before sleep, according to certain embodiments of the present disclosure. After the start (101), a processing unit determines whether glucose readings (105) exceed a threshold. (310) If not, the processing unit repeats step 310 until it receives a glucose reading exceeding the threshold. If a glucose reading exceeds the threshold, the processing unit next determines if the glucose reading was generated within a certain amount of time before expected sleep onset. (312) If steps 310 and 312 (each representing a glucose criterion) are satisfied, then the user exhibits the glucose state for purposes of method 300. If the glucose reading exceeding the threshold was not generated within the specified time period, processing returns to step 310 until a glucose reading exceeding the threshold is received. If the threshold-exceeding glucose reading is received within the specified time period, the processing unit then determines whether acceleration readings (115) indicate an activity level less than an activity threshold. (320) An activity level below the threshold is the criterion for the activity state in this embodiment (300). The activity threshold may be set, for example, to distinguish sleep, or pre-sleep activities, from more vigorous activities performed at other times of day. If the acceleration readings indicate an activity level above the activity threshold, processing returns to step 310 until a glucose reading exceeding the threshold is received. If the activity level is below threshold (indicating the activity state), the processing unit then determines whether the activity state coincides with the glucose state. (130) If not, processing returns to step 310 until a glucose reading above the glucose threshold is detected. If the glucose state and the activity state coincide, the processing unit sends a message to a user interface indicating that the user should refrain from eating soon before sleep. (340) In some embodiments the processing unit sends the message within T time (a critical amount of time) of the later-occurring of the glucose state or the activity state. Sending the message to the user interface within the critical amount of time may ensure timely presentation of the message and maximize its effectiveness. After the processing unit sends the message to the user interface (340), the method (300) ends. (199)

Glucose levels above certain thresholds (hyperglycemia) may be harmful. However, by the time glucose levels exceed the threshold, food already in the gut may cause the glucose levels to continue increasing far above the threshold. It would be advantageous to forestall hyperglycemia before it occurs. For this reason, some embodiments use a threshold for the rate of change (or higher derivatives) of glucose level as a criterion to determine a glucose state. In the case of hyperglycemia, some embodiments may use an upper threshold on a positive rate of change (indicating increasing glucose levels) as a criterion for a glucose state. Some embodiments may use thresholds for both glucose level and the rate of change of the glucose level as criteria for the glucose state. This may distinguish beneficial glucose increases (as when the user is hypoglycemic) from detrimental glucose increases (as when glucose levels are in-range but increasing towards hyperglycemia). User activity may provide context as to whether glucose levels are unhealthy and, if so, what message to provide. If glucose levels are high but the user is engaged in physical activity, the physical activity may be sufficient to bring the user's glucose level down. If a glucose increase is accompanied by physical activity, the increase itself may be caused by the physical activity triggering, for example, glycogen breakdown. Thus, a combination of high and/or increasing glucose levels accompanied by little or no physical activity may trigger some embodiments to send a message to the user interface suggesting a behavior that would decrease or moderate glucose levels.

Figure 4:
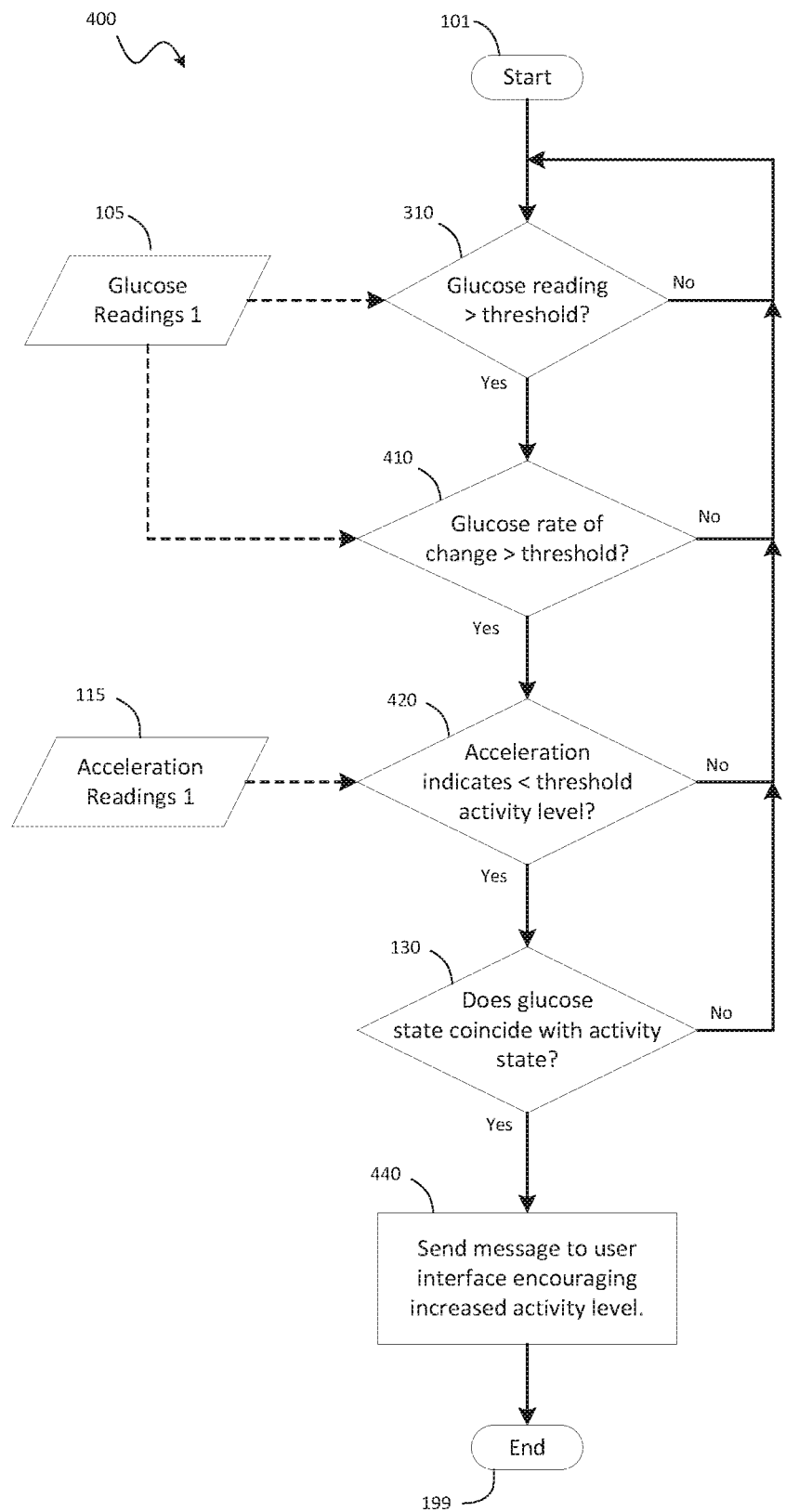
FIG. 4 presents a flowchart illustrating a method of regulating glucose levels using sensed data from a glucose monitor and an accelerometer to predict excessive glucose levels, according to certain embodiments of the present disclosure.

FIG. 4 presents a flowchart illustrating a method (400) of regulating glucose levels using sensed data from a glucose monitor and an accelerometer to predict excessive glucose levels, according to certain embodiments of the present disclosure. After the start (101), a processing unit determines whether glucose readings (105) exceed a threshold. (310) If not, processing returns to step 310 until a glucose reading exceeding the threshold is received. If a glucose reading does exceed the threshold, the processing unit next determines if the rate of change in glucose readings exceeds a second, rate-of-change threshold. (410) If not, processing returns to step 310 until a glucose reading exceeding the threshold is received. Steps 310 and 410 represent two criteria which, if both satisfied, indicate that the use is in a glucose state. If the glucose rate of change exceeds the rate threshold, the processing unit next determines whether acceleration readings (115) indicate an activity level that is less than a threshold activity level. (420) If not, processing returns to step 310 until a glucose reading exceeding the threshold is received. If the activity level is less than the threshold, the user is deemed to be in the activity state and the processing unit then determines whether the activity state coincides with the glucose state. (130) If not, processing returns to step 310 until a glucose reading above the glucose threshold is detected. If the glucose state and the activity state coincide, the processing unit sends a message to a user interface encouraging increased physical activity. (440) The method (400) then ends. (199)

Mirroring hyperglycemia, hypoglycemic glucose levels may be headed towards dangerously low levels by the time the glucose level itself has fallen below an optimal threshold. Accordingly, it would be advantageous to forestall hypoglycemia before it occurs. For this reason, some embodiments use a threshold for the rate of change (or higher order derivative) of glucose level as a criterion to determine a glucose state. In the case of hypoglycemia, some embodiments may use a lower threshold on a negative rate of change (indicating decreasing glucose levels) as a criterion for a glucose state. Some embodiments may use thresholds for both glucose level and rate of change of glucose level as criteria for the glucose state. This may distinguish circumstances beneficial glucose decreases (as when the user is hyperglycemic) from detrimental glucose decreases (as when glucose levels are in-range but decreasing towards hypoglycemia). User activity may provide context as to whether glucose levels are headed towards being undesirably low and, if so, what message to provide. If glucose levels are within range but the user is engaged in physical activity, the physical activity may be sufficient to bring the user's glucose level below the desired threshold. Thus, if a combination of low and/or decreasing glucose levels accompanied by higher than threshold levels of physical activity may trigger some embodiments to send a message to the user interface suggesting a behavior that would increase or moderate glucose levels.

FIG. 5 presents a flowchart illustrating a method (500) of regulating glucose levels using sensed data from a glucose monitor and an accelerometer to predict glucose deficiency, according to certain embodiments of the present disclosure. After the start (101), a processing unit determines whether glucose readings (105) are less than a threshold. (510) If not, processing returns to step 510 until the processing unit receives a glucose reading that is less than the threshold. If a glucose reading does fall below the threshold, the processing unit next determines if the rate of change in the glucose readings (105) is less than a second, rate-of-change threshold. (510) (In the context of predicting hypoglycemia, the threshold may be negative, indicating a decreasing glucose level.) If the rate of change does not fall below the rate threshold, processing returns to step 510 until the processing unit receives a glucose reading that is less than the threshold. Steps 510 and 512 represent two criteria which, if both satisfied, indicate that the use is in a glucose state. If the glucose rate of change is less than the rate threshold, the processing unit next determines whether acceleration readings (115) indicate an activity level that is greater than a threshold activity level. (520) If not, processing returns to step 510 until the processing unit receives a glucose reading that is less than the glucose threshold. If the activity level is greater than the activity threshold, the user is in the activity state and the processing unit then determines whether the activity state coincides with the glucose state. (130) If not, processing returns to step 510 until the processing unit receives a glucose reading that is less than the threshold. If the glucose state and the activity state coincide, the processing unit sends a message to a user interface encouraging the user to consume carbohydrates. (540) The method (500) then ends. (199)

Some embodiments of the method automatically optimize performance for individual users. Optimization may take the form of identifying multiple instances in which a first glucose state and a first activity state coincide and comparing results (in the form of glucose readings and/or acceleration readings) after each instance. Some embodiments provide different outputs or output characteristics after each of the similar instances and select a preferred output or output characteristic based on the comparison of the results. The processing unit may send the preferred output or use the output characteristic after subsequent instances in which the first glucose state coincides with the first activity state. Some embodiments may use results gathered after the similar instances to modify the glucose criteria determining the glucose state and/or modify the acceleration criteria determining the activity state.

Figure 6A:
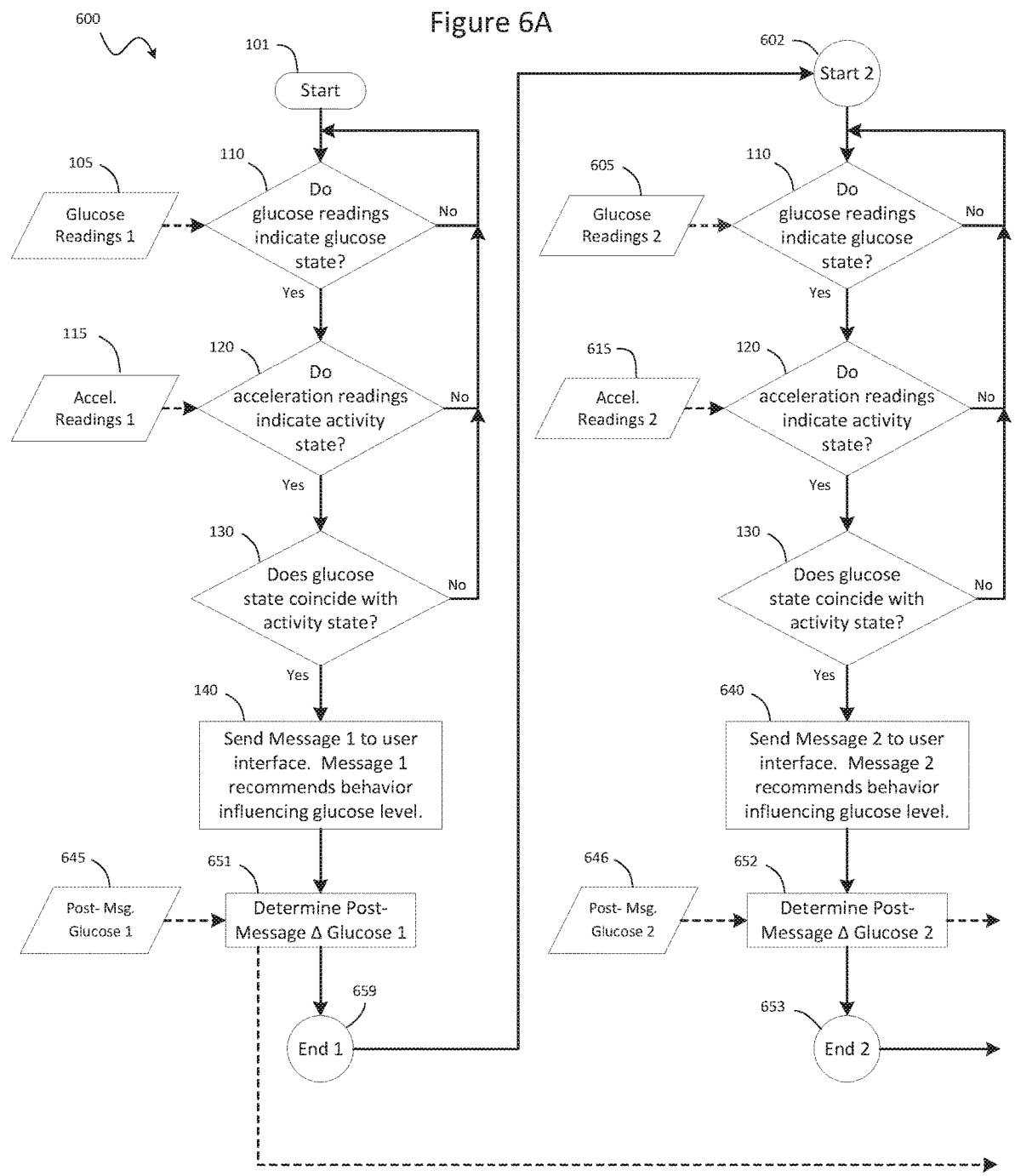
FIGS. 6A and 6B, combined, present a flowchart illustrating a method of regulating glucose levels using sensed data from a glucose monitor and an accelerometer in which messaging is selected using glucose changes observed after delivery of previous messages, according to certain embodiments of the present disclosure.
Figure 6B:
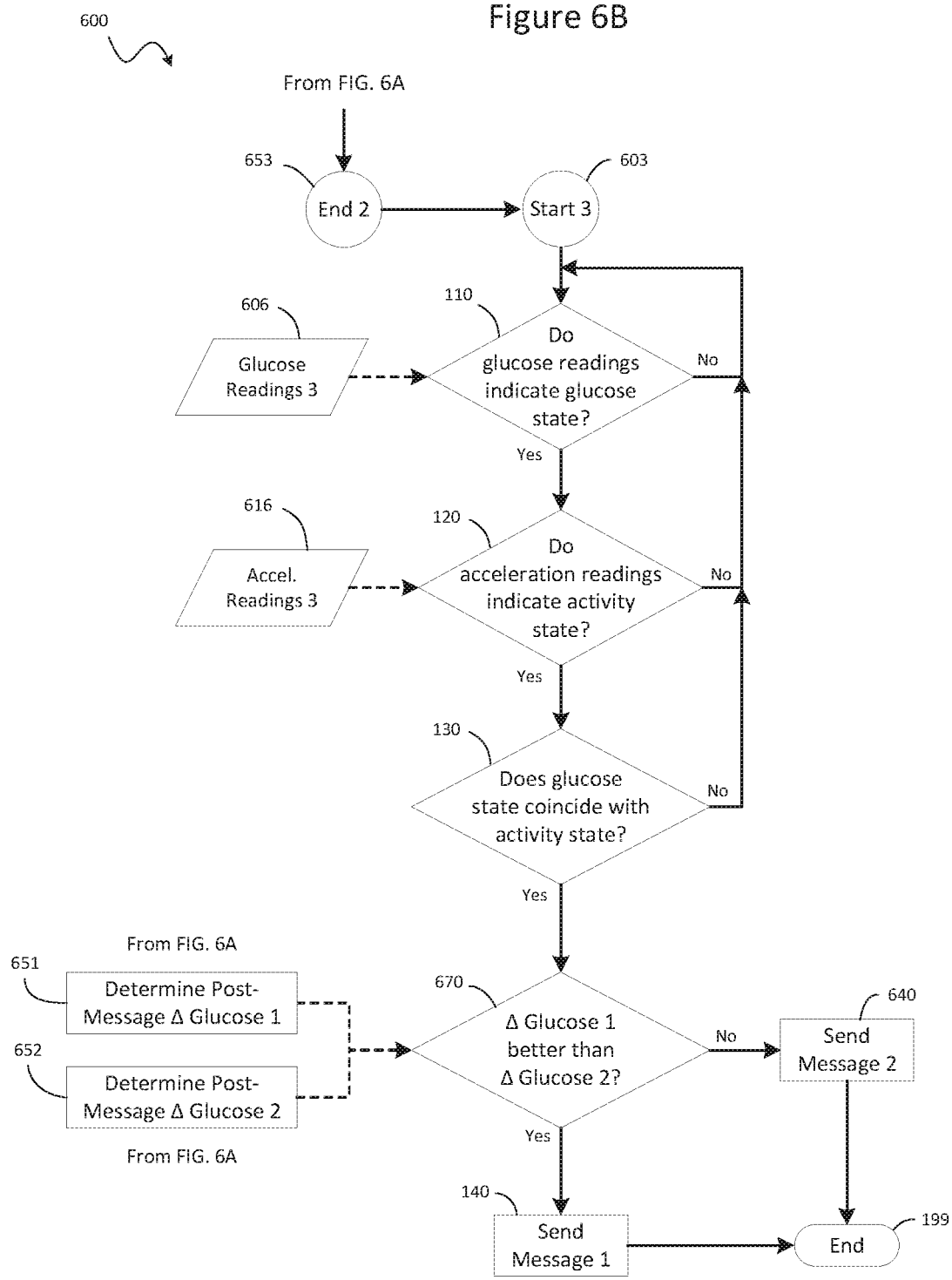

FIGS. 6A and 6B, combined, present a flowchart illustrating a method (600) of regulating glucose levels using sensed data from a glucose monitor and an accelerometer in which messaging is selected using glucose changes observed after delivery of previous messages, according to certain embodiments of the present disclosure. In FIG. 6A, after the start (101) of a first time period, a processing unit determines whether a first set of glucose readings (105) indicates that the user is in a glucose state. (110) If not, the processing unit repeats step 110 until it detects the glucose state. If the glucose state is detected, the processing unit then determines whether a first set of acceleration readings (115) indicates that the user is in an activity state. (120) If not, processing returns to step 110 to determine whether glucose readings indicate the glucose state. If the activity state is detected, the processing unit then determines whether the activity state coincides with the glucose state. (130) If not, processing returns to step 110 until the glucose state is detected. If the glucose state and the activity state coincide, the processing unit sends a first message to a user interface. (140) The message recommends performing or abstaining from an activity that affects the user's glucose level. After sending the message (140), the processing unit receives a first set of post-message glucose readings (645) and determines a change in glucose levels occurring after sending the first message. (651) The first time period ends at 659.

In FIG. 6A, after the start (602) of a second time period, the processing unit determines whether a second set of glucose readings (605) indicates that the user is in the glucose state. (110) If not, the processing unit repeats step 110 until it detects the glucose state. If the glucose state is detected, the processing unit then determines whether a second set of acceleration readings (615) indicates that the user is in an activity state. (120) If not, processing returns to step 110 to determine whether glucose readings indicate the glucose state. If the activity state is detected, the processing unit then determines whether the activity state coincides with the glucose state. (130) If not, processing returns to step 110 until the glucose state is detected. If the glucose state and the activity state coincide, the processing unit sends a second message to the user interface. (640) The message recommends performing or abstaining from an activity that affects the user's glucose level and is different in content or characteristic from the first message. After sending the message (640), the processing unit receives a second set of post-message glucose readings (646) and determines a change in glucose levels occurring after sending the second message. (652) The second time period ends at 653.

In FIG. 6B, after the start (603) of a third time period, the processing unit determines whether a third set of glucose readings (606) indicates that the user is in the glucose state. (110) If not, the processing unit repeats step 110 until it detects the glucose state. If the glucose state is detected, the processing unit then determines whether a second set of acceleration readings (616) indicates that the user is in an activity state. (120) If not, processing returns to step 110 to determine whether glucose readings indicate the glucose state. If the activity state is detected, the processing unit then determines whether the activity state coincides with the glucose state. (130) If not, processing returns to step 110 until the glucose state is detected. If the glucose state and the activity state coincide, the processing unit determines whether the change in glucose level after sending the first message (determined at 651) is better than the change in glucose level after sending the second message (determined at 652). (670) Which of those changes is better depends on whether the glucose state and activity state indicate a need for increased glucose levels or decreased glucose levels. If the user requires increased glucose levels, the greater of the two post-message glucose increases would be preferred (unless the increase was too great, bringing glucose levels above desired thresholds). Likewise, if the user requires decreased glucose levels, the greater of the two post-message glucose decreases would be preferred (unless the decrease was too great, bringing glucose levels below desired thresholds). If the change in the first post-message glucose level is better than the change in the second post-message glucose levels, the processing unit sends the first message to the user interface. (140) If the change in the first post-message glucose levels is not better than the change in the second post-message glucose levels, the processing unit sends the second message to the user interface. (640) After sending either the first message or the second message, the method (600) ends. (199)

Figure 7:
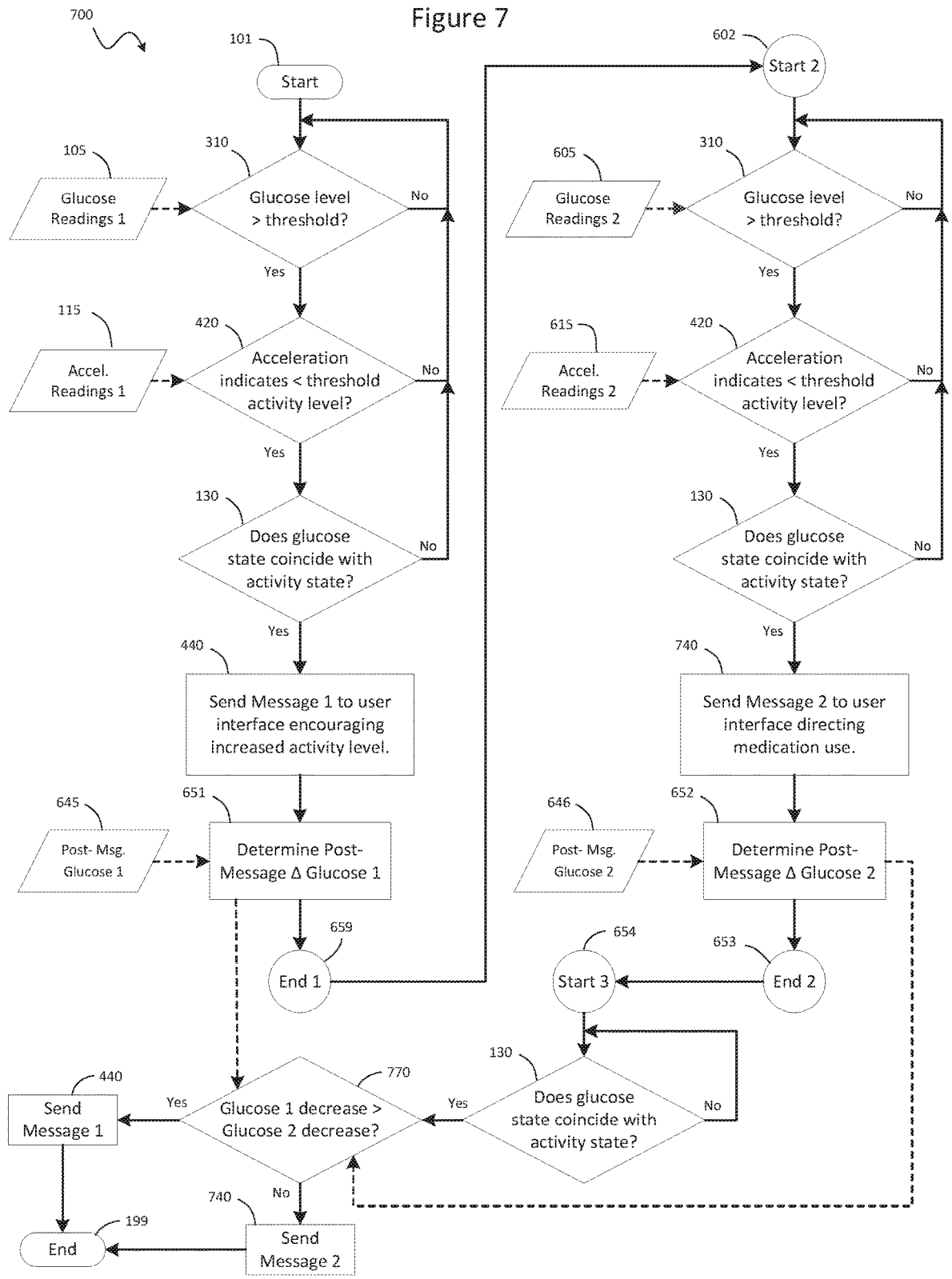
FIG. 7 presents a flowchart illustrating a method of regulating glucose levels using sensed data from a glucose monitor and an accelerometer in which messaging is selected by comparing glucose decreases after delivery of messages directing different methods of decreasing glucose, according to certain embodiments of the present disclosure.

FIG. 7 presents a flowchart illustrating a method (700) of regulating glucose levels using sensed data from a glucose monitor and an accelerometer in which messaging is selected by comparing glucose decreases after delivery of messages directing different methods of decreasing glucose, according to certain embodiments of the present disclosure. After the start (101) of a first time period, a processing unit determines whether any of a first set of glucose readings (105) exceeds a glucose threshold. (310) If not, the processing unit repeats step 310 until it detects a glucose reading that exceeds the glucose threshold. If one of the glucose readings (105) does exceed the glucose threshold, the criterion for the glucose state is satisfied and the processing unit then determines whether a first set of acceleration readings (115) indicates an activity level that is below a threshold activity level. (420) If not, the processing unit repeats step 310 until it detects a glucose reading that exceeds the glucose threshold. If the activity level is below the threshold activity level, the criterion for the activity state has been satisfied and the processing unit then determines whether the activity state coincides with the glucose state. (130) If not, the processing unit repeats step 310 until it detects a glucose reading that exceeds the glucose threshold. If the glucose state and the activity state coincide, the processing unit sends a first message to a user interface recommending increased activity levels. (440) After sending the message (440), the processing unit receives a first set of post-message glucose readings (645) and determines a change in glucose levels occurring after sending the first message. (651) The first time period ends at 659.

A second time period in FIG. 7 starts at 602. The processing unit determines whether any of a second set of glucose readings (605) exceeds the glucose threshold. (310) If not, the processing unit repeats step 310 until it detects a glucose reading that exceeds the glucose threshold. If one of the glucose readings (605) does exceed the glucose threshold, the criterion for the glucose state is satisfied and the processing unit then determines whether a second set of acceleration readings (615) indicates an activity level that is below a threshold activity level. (420) If not, the processing unit repeats step 310 until it detects a glucose reading that exceeds the glucose threshold. If the activity level is below the threshold activity level, the criterion for the activity state has been satisfied and the processing unit then determines whether the activity state coincides with the glucose state. (130) If not, the processing unit repeats step 310 until it detects a glucose reading that exceeds the glucose threshold. If the glucose state and the activity state coincide, the processing unit sends a second message to a user interface directing medication use (of an anti-hyperglycemic drug). (740) After sending the message (740), the processing unit receives a second set of post-message glucose readings (646) and determines a change in glucose levels occurring after sending the second message. (652) The second time period ends at 653.

A third time period in FIG. 7 starts at 654. As with the first and second time periods, the processing unit executes steps 310 (on a third set of glucose readings) and 420 (on a third set of acceleration readings). However, to fit the method (700) on a single sheet, the third instance of steps 310 and 420 are not shown and are implied in step 130, in which the processing unit determines whether, during the third time period, the glucose state and the activity state coincide. (130) If not, the processing unit repeats step 310 (not shown) until it detects a glucose reading that exceeds the glucose threshold. If the glucose state and activity state coincide, the processing unit next determines whether the glucose decrease after the first message (determined at 651) was greater than the glucose decrease after the second message (determined at 652). (770) If the glucose decrease after the first message was greater than the glucose decrease after the second message, the processing unit sends the first message to the user interface. (440) If the glucose decrease after the first message was not greater than the glucose decrease after the second message, the processing unit sends the second message to the user interface. (740) The method (700) then ends. (199)

Two messages may recommend the same type of method for altering glucose levels (e.g. physical activity or medication use) but differ as to other aspects such as the timing, amount, or intensity. For example, two messages may both recommend taking an anti-hyperglycemic drug, but the messages may differ in the recommended dosage. As a second example, two messages may each recommend physical activity, but one may recommend starting immediately while another may recommend starting in thirty minutes. Individuals may differ in their responses to a given amount of medication or physical activity and tailoring recommendations as to timing, quantity, or other characteristics to particular individuals can help each optimize his or her glycemic control.

Figure 8:
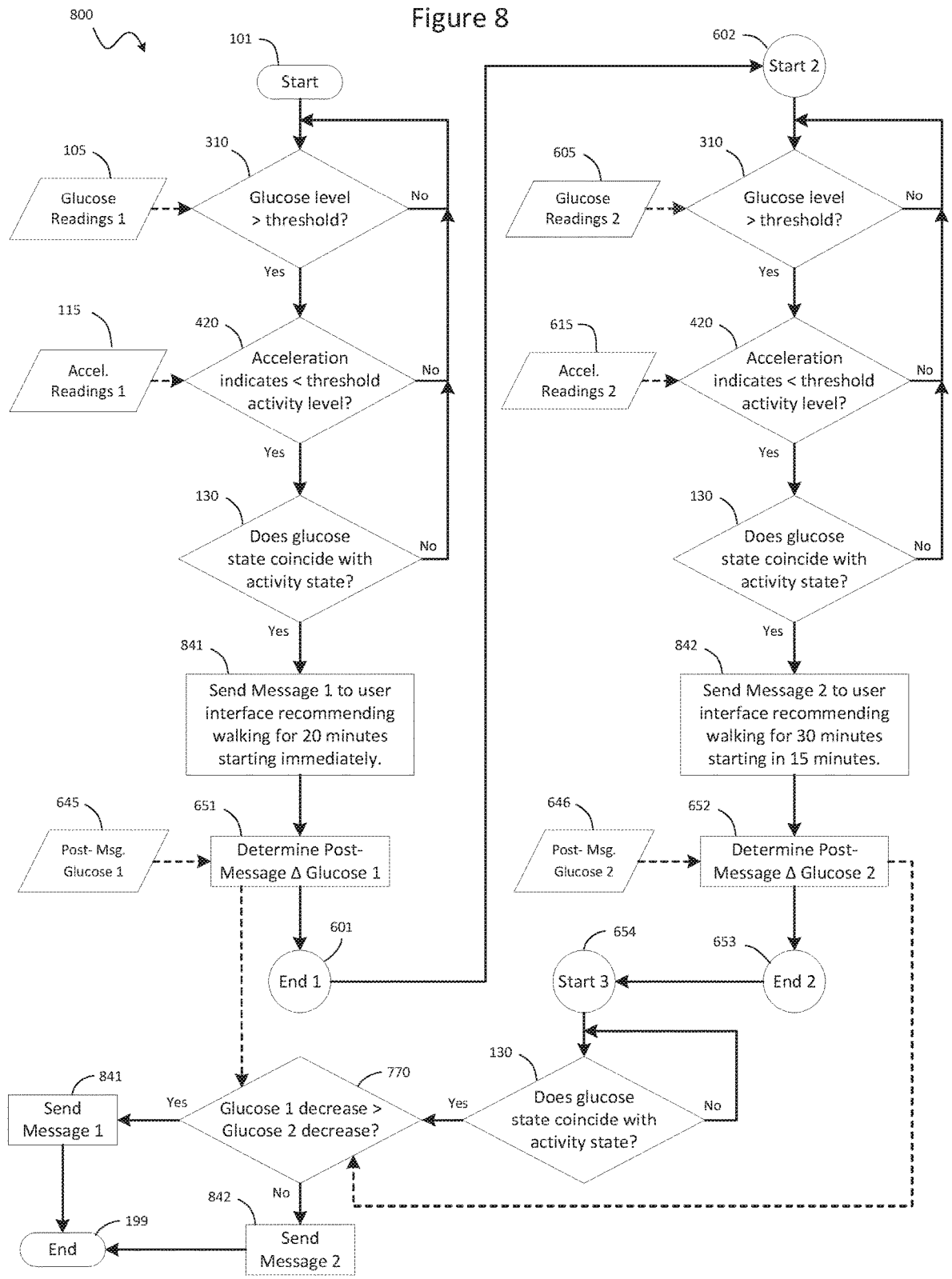
FIG. 8 presents a flowchart illustrating a method of regulating glucose levels using sensed data from a glucose monitor and an accelerometer in which messaging is selected by comparing glucose decreases after delivery of messages directing different timing of physical activity, according to certain embodiments of the present disclosure.

FIG. 8 presents a flowchart illustrating a method (800) of regulating glucose levels using sensed data from a glucose monitor and an accelerometer in which messaging is selected by comparing glucose decreases after delivery of messages directing different timing of physical activity, according to certain embodiments of the present disclosure. After the start (101) of a first time period, a processing unit determines whether any of a first set of glucose readings (105) exceeds a glucose threshold. (310) If not, the processing unit repeats step 310 until it detects a glucose reading that exceeds the glucose threshold. If one of the glucose readings (105) does exceed the glucose threshold, the criterion for the glucose state is satisfied and the processing unit then determines whether a first set of acceleration readings (115) indicates an activity level that is below a threshold activity level. (420) If not, the processing unit repeats step 310 until it detects a glucose reading that exceeds the glucose threshold. If the activity level is below the threshold activity level, the criterion for the activity state has been satisfied and the processing unit then determines whether the activity state coincides with the glucose state. (130) If not, the processing unit repeats step 310 until it receives a glucose reading that exceeds the glucose threshold. If the glucose state and the activity state coincide, the processing unit sends a first message to a user interface recommending that the user start walking immediately and walk for 20 minutes. (841) After sending the first message (841), the processing unit receives a first set of post-message glucose readings (645) and determines a change in glucose levels occurring after sending the first message. (651) The first time period ends at 659.

A second time period in FIG. 8 starts at 602. The processing unit determines whether any of a second set of glucose readings (605) exceeds the glucose threshold. (310) If not, the processing unit repeats step 310 until it detects a glucose reading that exceeds the glucose threshold. If one of the glucose readings (605) does exceed the glucose threshold, the criterion for the glucose state is satisfied and the processing unit then determines whether a second set of acceleration readings (615) indicates an activity level that is below a threshold activity level. (420) If not, the processing unit repeats step 310 until it detects a glucose reading that exceeds the glucose threshold. If the activity level is below the threshold activity level, the criterion for the activity state has been satisfied and the processing unit then determines whether the activity state coincides with the glucose state. (130) If not, the processing unit repeats step 310 until it detects a glucose reading that exceeds the glucose threshold. If the glucose state and the activity state coincide, the processing unit sends a second message to a user interface recommending that the user walk for 30 minutes starting in 15 minutes. (842) After sending the second message (842), the processing unit receives a second set of post-message glucose readings (646) and determines a change in glucose levels occurring after sending the second message. (652) The second time period ends at 653.

A third time period in FIG. 8 starts at 654. As with the first and second time periods, the processing unit executes steps 310 (on a third set of glucose readings) and 420 (on a third set of acceleration readings). However, to fit the method (800) on a single sheet, the third instance of steps 310 and 420 are not shown and are implied in step 130, in which the processing unit determines whether, during the third time period, the glucose state and the activity state coincide. (130) If not, the processing unit repeats step 310 (not shown) until it detects a glucose reading that exceeds the glucose threshold. If the glucose state and activity state coincide, the processing unit next determines whether the glucose decrease after the first message (determined at 651) was greater than the glucose decrease after the second message (determined at 652). (770) If the glucose decrease after the first message was greater than the glucose decrease after the second message, the processing unit sends the first message to the user interface. (841) If the glucose decrease after the first message was not greater than the glucose decrease after the second message, the processing unit sends the second message to the user interface. (842) The method (800) then ends. (199)

In addition to differing in their content, messages may also differ in their characteristics. Two messages may differ in their attributes, even if their content is identical. Characteristics of a message may include, for example, when it is sent relative to the coincidence of the glucose state and the activity state, when it is sent as a time of day, font size of the message (if the user interface is a display screen), or volume (if the user interface is an audio speaker). Differences in message attributes may influence their effectiveness in influencing the user to engage in or refrain from behaviors that control glucose levels.

Figure 9:
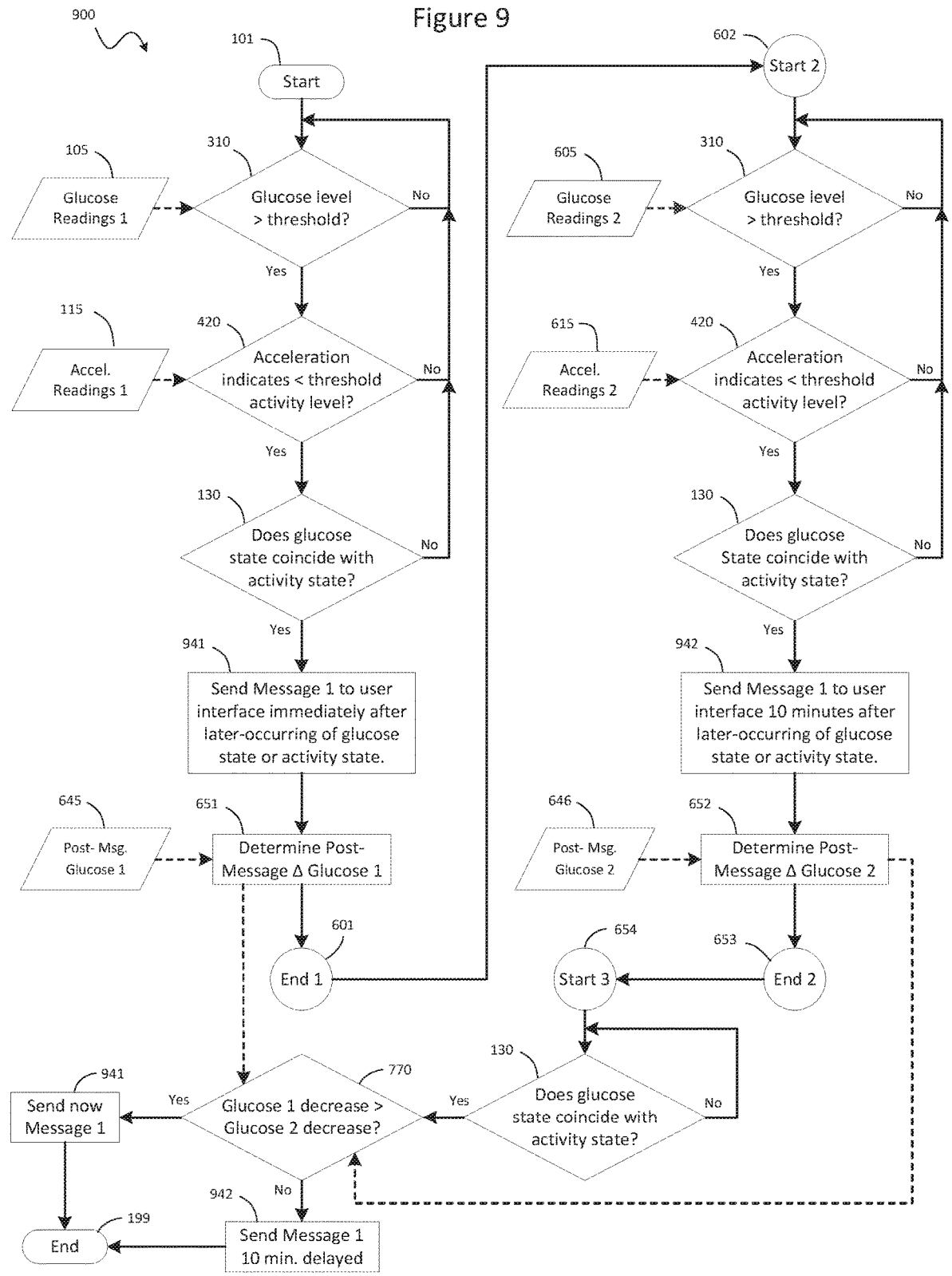
FIG. 9 presents a flowchart illustrating a method of regulating glucose levels using sensed data from a glucose monitor and an accelerometer in which messaging is selected by comparing glucose decreases after delivery of messages delivered at two different times, according to certain embodiments of the present disclosure.

FIG. 9 presents a flowchart illustrating a method (900) of regulating glucose levels using sensed data from a glucose monitor and an accelerometer in which messaging is selected by comparing glucose decreases after delivery of messages delivered at two different times, according to certain embodiments of the present disclosure. After the start (101) of a first time period, a processing unit determines whether any of a first set of glucose readings (105) exceeds a glucose threshold. (310) If not, the processing unit repeats step 310 until it detects a glucose reading that exceeds the glucose threshold. If one of the glucose readings (105) does exceed the glucose threshold, the criterion for the glucose state is satisfied and the processing unit then determines whether a first set of acceleration readings (115) indicates an activity level that is below a threshold activity level. (420) If not, the processing unit repeats step 310 until it detects a glucose reading that exceeds the glucose threshold. If the activity level is below the threshold activity level, the criterion for the activity state has been satisfied and the processing unit then determines whether the activity state coincides with the glucose state. (130) If not, the processing unit repeats step 310 until it detects a glucose reading that exceeds the glucose threshold. If the glucose state and the activity state coincide, the processing unit sends a first message to a user interface immediately after the later-occurring of the onset of the glucose state or the onset of the activity state. (941) The first message may recommend an activity (or refraining from any activity) that would moderate high glucose levels. After sending the message (941), the processing unit receives a first set of post-message glucose readings (645) and determines a change in glucose levels occurring after sending the first message. (651) The first time period ends at 659.

A second time period in FIG. 9 starts at 602. The processing unit determines whether any of a second set of glucose readings (605) exceeds the glucose threshold. (310) If not, the processing unit repeats step 310 until it detects a glucose reading that exceeds the glucose threshold. If one of the glucose readings (605) does exceed the glucose threshold, the criterion for the glucose state is satisfied and the processing unit then determines whether a second set of acceleration readings (615) indicates an activity level that is below a threshold activity level. (420) If not, the processing unit repeats step 310 until it detects a glucose reading that exceeds the glucose threshold. If the activity level is below the threshold activity level, the criterion for the activity state has been satisfied and the processing unit then determines whether the activity state coincides with the glucose state. (130) If not, the processing unit repeats step 310 until it detects a glucose reading that exceeds the glucose threshold. If the glucose state and the activity state coincide, the processing unit sends the first message to the user interface 10 minutes after the later occurring of the onset of the glucose state or the onset of the activity state. (942) Note that the content of the message sent during the second time period (at 942) may be identical to the content of the message during the first time period (at 941) and that the two messages may differ only as to the times that they are sent relative to the coincidence of the glucose state and that activity state. After sending the message (942), the processing unit receives a second set of post-message glucose readings (646) and determines a change in glucose levels occurring after sending the second message. (652) The second time period ends at 653.

A third time period in FIG. 9 starts at 654. As with the first and second time periods, the processing unit executes steps 310 (on a third set of glucose readings) and 420 (on a third set of acceleration readings). However, to fit the method (900) on a single sheet, the third instance of steps 310 and 420 are not shown and are implied in step 130, in which the processing unit determines whether, during the third time period, the glucose state and the activity state coincide. (130) If not, the processing unit repeats step 310 (not shown) until it detects a glucose reading that exceeds the glucose threshold. If the glucose state and activity state coincide, the processing unit next determines whether the glucose decrease after sending the first message immediately (determined at 651) was greater than the glucose decrease after the first message 10 minutes delayed (determined at 652). (770) If the glucose decrease after the first message sent immediately was greater than the glucose decrease after the 10-minute delayed first message, the processing unit sends the first message to the user interface immediately. (941) If the glucose decrease after the first message sent immediately was not greater than the glucose decrease after the delayed first message, the processing unit sends the first message to the user interface 10 minutes after the coincidence of the first glucose state and the first activity state. (942) The method (900) then ends. (199) While the messages sent during the first time period and second time period are identical in content, the differences in their timing may allow them to be viewed as two distinct messages, fitting the framework illustrated in FIGS. 6A and 6B.

Some embodiments compare post-message acceleration readings after multiple instances in which a first glucose state coincides with a first activity state. If the message sent to the user interface recommends that the user to perform or refrain from physical activity, monitoring post-message acceleration readings may inform the processing unit as to whether the user complied with the recommendation. If the accelerometer generating the acceleration readings is coupled to the wrist, arm, or hand of the user, more sophisticated processing may determine whether the user's movements are indicative of eating, and thereby determine whether the user complied with a message recommending eating or refraining from eating.

Figure 10:
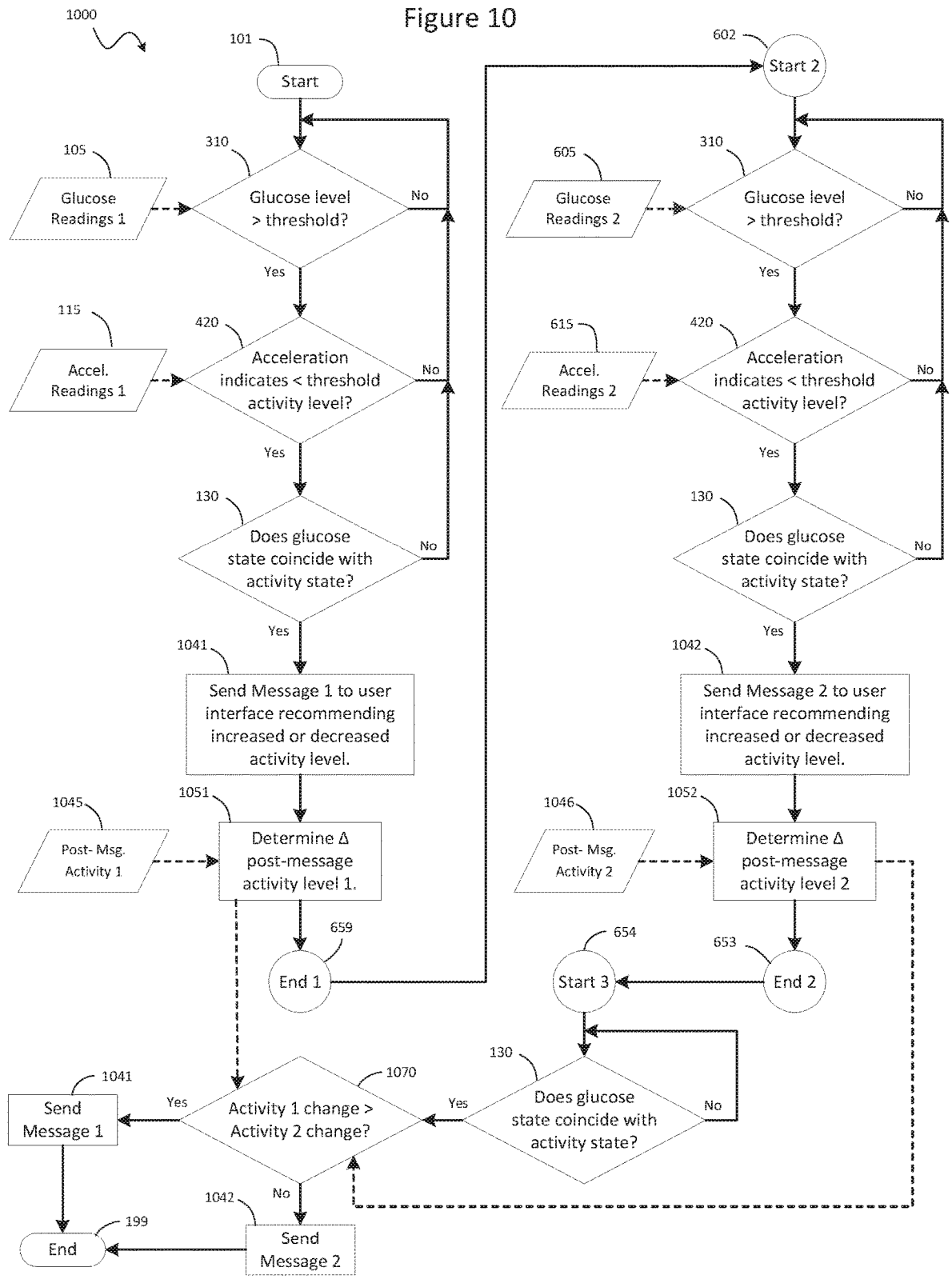
FIG. 10 presents a flowchart illustrating a method of regulating glucose levels using sensed data from a glucose monitor and an accelerometer in which messaging is selected by comparing activity changes after delivery of different messages directing altered activity, according to certain embodiments of the present disclosure.

FIG. 10 presents a flowchart illustrating a method (1000) of regulating glucose levels using sensed data from a glucose monitor and an accelerometer in which messaging is selected by comparing activity changes after delivery of two messages directing altered activity, according to certain embodiments of the present disclosure. After the start (101) of a first time period, a processing unit determines whether any of a first set of glucose readings (105) exceeds a glucose threshold. (310) If not, the processing unit repeats step 310 until it detects a glucose reading that exceeds the glucose threshold. If one of the glucose readings (105) does exceed the glucose threshold, the criterion for the glucose state is satisfied and the processing unit then determines whether a first set of acceleration readings (115) indicates an activity level that is below a threshold activity level. (420) If not, the processing unit repeats step 310 until it detects a glucose reading that exceeds the glucose threshold. If the activity level is below the threshold activity level, the criterion for the activity state has been satisfied and the processing unit then determines whether the activity state coincides with the glucose state. (130) If not, the processing unit repeats step 310 until it detects a glucose reading that exceeds the glucose threshold. If the glucose state and the activity state coincide, the processing unit sends a first message to a user interface recommending either an increased or decreased activity level. (1041) After sending the message (1041), the processing unit receives a first set of post-message acceleration readings (1045) and determines a change in activity levels occurring after sending the first message. (1051) The first time period ends at 659.

A second time period in FIG. 10 starts at 602. The processing unit determines whether any of a second set of glucose readings (605) exceeds the glucose threshold. (310) If not, the processing unit repeats step 310 until it detects a glucose reading that exceeds the glucose threshold. If one of the glucose readings (605) does exceed the glucose threshold, the criterion for the glucose state is satisfied and the processing unit then determines whether a second set of acceleration readings (615) indicates an activity level that is below a threshold activity level. (420) If not, the processing unit repeats step 310 until it detects a glucose reading that exceeds the glucose threshold. If the activity level is below the threshold activity level, the criterion for the activity state has been satisfied and the processing unit then determines whether the activity state coincides with the glucose state. (130) If not, the processing unit repeats step 310 until it detects a glucose reading that exceeds the glucose threshold. If the glucose state and the activity state coincide, the processing unit sends a second message to the user interface encouraging an increased or decreased activity level. (1042) The first message and second message may differ in content or at least one characteristic. After sending the second message (1042), the processing unit receives a second set of post-message acceleration readings (1046) and determines a change in activity levels occurring after sending the second message. (1052) The second time period ends at 653.

A third time period in FIG. 10 starts at 654. As with the first and second time periods, the processing unit executes steps 310 (on a third set of glucose readings) and 420 (on a third set of acceleration readings). However, to fit the method (1000) on a single sheet, the third instance of steps 310 and 420 are not shown and are implied in step 130. The processing unit determines whether, during the third time period, the glucose state and the activity state coincide. (130) If not, the processing unit repeats step 310 (not shown) until it detects a glucose reading that exceeds the glucose threshold. If the glucose state and activity state coincide, the processing unit next determines whether the activity change after the first message (determined at 1051) was greater than or less than the activity change after the second message (determined at 1052). (1070) The direction of the changes compared in step 1070 depends on whether the first message and the second message recommend an increased activity level or a decreased activity level. If the first message and the second message both recommended increased activity, step 1070 would determine whether the activity increase after the first message was greater than the activity message after the second message. Conversely, if the first message and the second message both recommended a decreased activity level, step 1070 would determine whether the decrease in activity level after the first message was greater than the decrease in activity level after the second message. If the activity change (in the desired direction) after the first message was greater than the activity change (in the desired direction) after the second message, the processing unit sends the first message to the user interface. (1041) If the activity change (in the desired direction) after the first message was not greater than the activity change (in the desired direction) after the second message, the processing unit sends the second message to the user interface. (1042) The method (1000) then ends. (199)

In addition to improving messaging, some embodiments use information obtained from glucose readings and acceleration readings to alter the glucose criteria defining the glucose state and/or the acceleration criteria defining the activity state. It is understood that the phrase "glucose criteria" encompasses embodiments in which there is only a single glucose criterion and that the phrase "acceleration criteria" encompasses embodiments in which there is only a single acceleration criterion. When the glucose criteria for a first glucose state are altered and the altered glucose criteria are satisfied, the user may be referred to as being in a second glucose state because the first glucose state was defined by the unaltered glucose criteria. Similarly, when the acceleration criteria for a first activity state are altered and the altered acceleration criteria are satisfied, the user may be referred to as being in a second activity state because the first activity state was defined by the unaltered acceleration criteria. Some embodiments generate a model describing the relationship between the glucose readings and the acceleration readings of an individual and use the model to alter the glucose criteria defining the relevant glucose state and/or the acceleration criteria defining the relevant activity state. For example, some embodiments may start with a glucose criterion that is satisfied if a glucose reading exceeds a first glucose threshold that is based on population-based model describing the relationship between glucose level and acceleration. As the processing unit receives glucose readings and acceleration readings from the user, it may generate a model describing the relationship between glucose and acceleration for the individual which, in turn, may be used to alter the glucose threshold level of the glucose criterion defining the glucose state to better match the physiology of the individual user.

Figure 11:
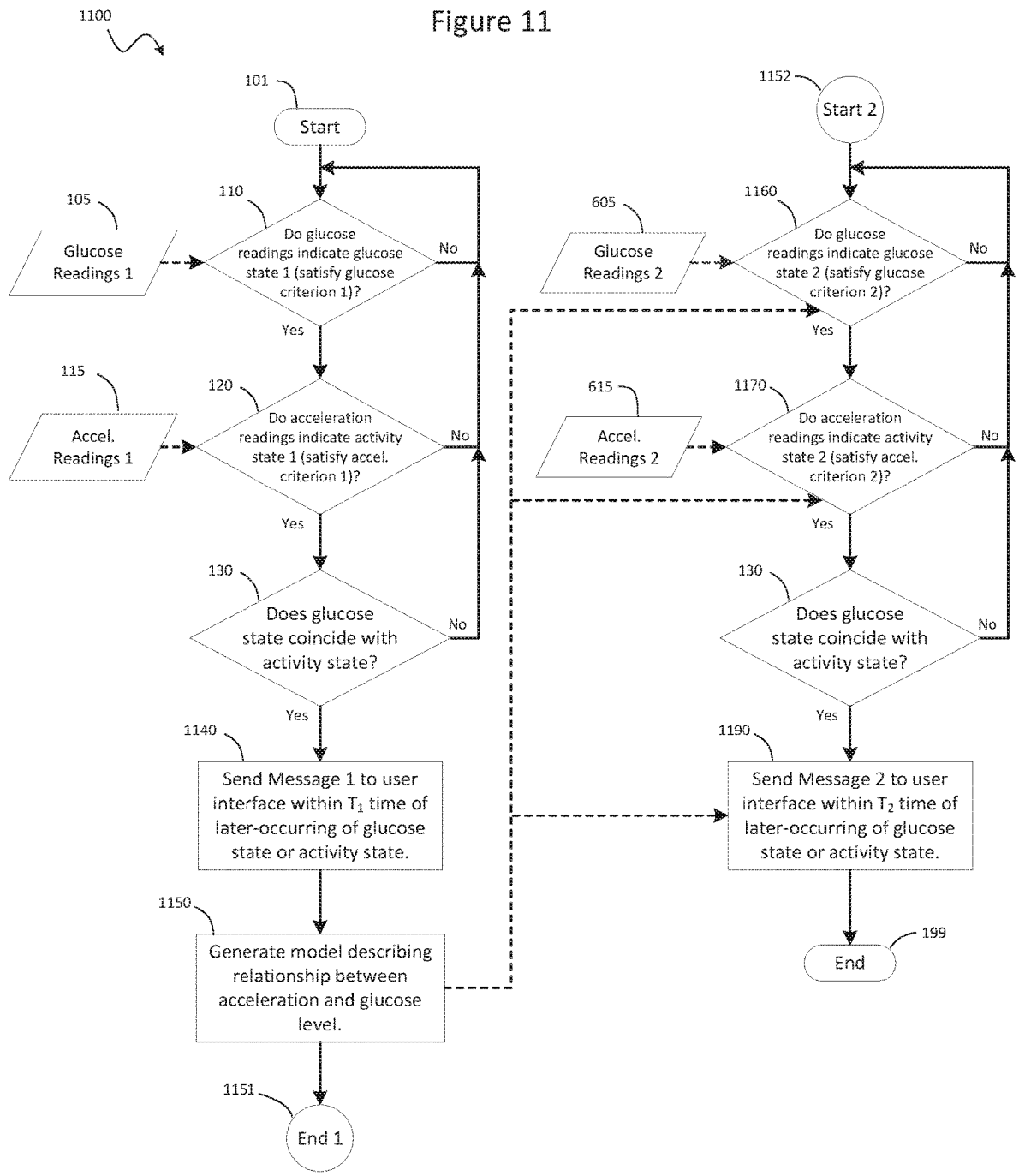
FIG. 11 presents a flowchart illustrating a method of regulating glucose levels using sensed data from a glucose monitor and an accelerometer in which a processing unit generates a model describing a relationship between acceleration and glucose level according to certain embodiments of the present disclosure.

FIG. 11 presents a flowchart illustrating a method (1100) of regulating glucose levels using sensed data from a glucose monitor and an accelerometer in which a processing unit generates a model describing a relationship between acceleration and glucose level according to certain embodiments of the present disclosure. After the start of a first time period (101), a processing unit determines whether a first set of glucose readings (105) satisfies a first set of glucose criteria, thereby indicating that the user is in a first glucose state. (110) If not, processing repeats step 110 until the processing unit detects the first glucose state. If the first glucose state is detected, the processing unit then determines whether a first set of acceleration readings (115) satisfies a first set of acceleration criteria, thereby indicating that the user is in a first activity state. (120) If not, processing returns to step 110 to determine whether glucose readings indicate the first glucose state. If the first activity state is detected, the processing unit then determines whether the first activity state coincides with (occurs at the same time as) the first glucose state. (130) If not, processing returns to step 110 until the first glucose state is detected. If the first glucose state and the first activity state coincide, the processing unit sends a message to a user interface within a first critical amount of time ($T_1$) after the first time at which the first glucose state and first activity state first coincide. (1140) The message may recommend performing or abstaining from an activity that affects the user's glucose level. Using the first set of glucose readings (105) and the first set of acceleration readings (115), the processing unit generates a model describing the relationship between glucose levels and activity of the user. (1150) The first time period ends at 1151.

After the start of a second time period for FIG. 11 (1152), a processing unit determines whether a second set of glucose readings (605) satisfies a second set of glucose criteria, thereby indicating that the user is in a second glucose state. (1160) The second set of glucose criteria may be selected using the model generated at step 1150. If the second glucose state is not detected, processing repeats step 1160 until the processing unit detects the second glucose state. If the second glucose state is detected, the processing unit then determines whether a second set of acceleration readings (615) satisfies a second set of acceleration criteria, thereby indicating that the user is in a second activity state. (1170) The second set of acceleration criteria may be chosen using the model generated at step 1150. If the second activity state is not detected, processing returns to step 1160 to determine whether glucose readings indicate the second glucose state. If the second activity state is detected, the processing unit then determines whether the second activity state coincides with the second glucose state. (130) If not, processing returns to step 1160 until the second glucose state is detected. If the second glucose state and the second activity state coincide, the processing unit sends a message to the user interface within a second critical amount of time ($T_2$) after the first time at which the second glucose state and second activity state first coincide. (1190) The second message may recommend performing or abstaining from an activity that affects the user's glucose level. $T_2$ may be selected using the model generated at step 1150. After the processing unit sends the second message to the user interface (1190), the method (1100) ends. (199)

In addition to glucose readings and acceleration readings, some embodiments may use user inputs to determine whether the user is in a glucose state or an activity state. Inputs are entered on a user interface capable of receiving user inputs. For example, user inputs could be entered through a touch screen, key pad, microphone, or camera. The user interface may then send the user input to the processing unit. User inputs may include, for example, information regarding user activities such as the timing, content, and quantity of foods or medications consumed or physical activity performed. Glucose criteria and/or acceleration criteria may include criteria regarding user inputs. For example, a glucose criterion or acceleration criterion may be influenced by whether a user input indicates that the user has recently consumed a meal. Messages or message attributes may also be selected based at least in part on user inputs. For example, a message timing may be altered based on content from user inputs.

Figure 12:
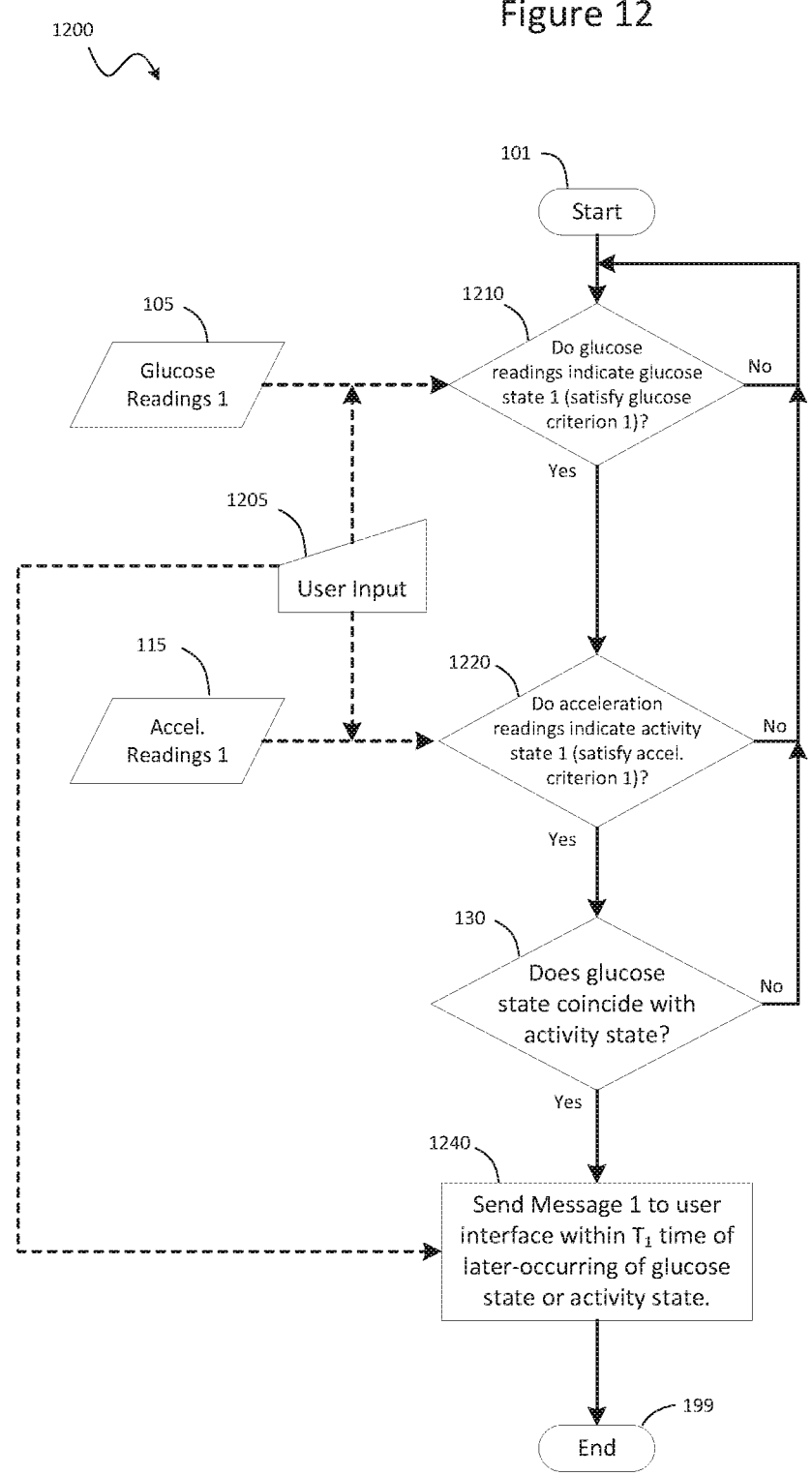
FIG. 12 presents a flowchart illustrating a method of regulating glucose levels using sensed data from a glucose monitor and an accelerometer and user inputs from a user interface according to certain embodiments of the present disclosure.

FIG. 12 presents a flowchart illustrating a method (1200) of regulating glucose levels using sensed data from a glucose monitor and an accelerometer and user inputs from a user interface according to certain embodiments of the present disclosure. After the start (101), a processing unit determines whether a set of glucose readings (105) satisfies a set of glucose criteria, thereby indicating that the user is in a glucose state. (1210) The set of glucose criteria may be determined, at least in part, from user inputs entered on a first user interface (1205). If the glucose state is not detected, the processing unit repeats step 1210 until it detects the glucose state. If the glucose state is detected, the processing unit then determines whether a set of acceleration readings (115) satisfies a set of acceleration criteria, thereby indicating that the user is in an activity state. (1220) The set of activity criteria may be determined, at least in part, from the user inputs entered on the first user interface (1205). If the activity state is not detected, processing returns to step 1210 to determine whether glucose readings indicate the glucose state. If the activity state is detected, the processing unit then determines whether the activity state coincides with the glucose state. (130) If not, the processing unit returns to step 1210 until it detects the glucose state. If the glucose state and the activity state coincide, the processing unit sends a message to a second user interface within a first critical amount of time ($T_1$) after the first time at which the first glucose state and first activity state coincide. (1240) The message recommends performing or abstaining from an activity that affects the user's glucose level. The message and/or $T_1$ may be selected based at least in part on the user input (1205) entered on the first user interface. The first user interface and the second user interface may be one and the same if the user interface is capable of both sending information to and receiving information from the user. For example, a touch-screen user interface could serve as both the first and second user interfaces. The method (1200) ends at 199.

Some embodiments may use a combination of glucose readings, acceleration readings, and user inputs to generate a model predicting user behaviors such as eating or taking medications. During a training phase, glucose readings and/or acceleration readings gathered around times that user inputs indicate the user is engaged in a particular behavior may be used to generate a model predicting the reported activity. After the training phase, glucose readings and/or acceleration readings, without user inputs, may be used to predict the previously-reported behavior of the user. These embodiments may be useful when used in conjunction with messages that recommend, for example, eating, taking medication, or refraining from either of those activities and may use glucose readings and/or acceleration readings to determine whether the user has complied with the message's recommendation. Such predictive models may also be useful in determining the best time to send a message or other attributes of the message.

Figure 13:
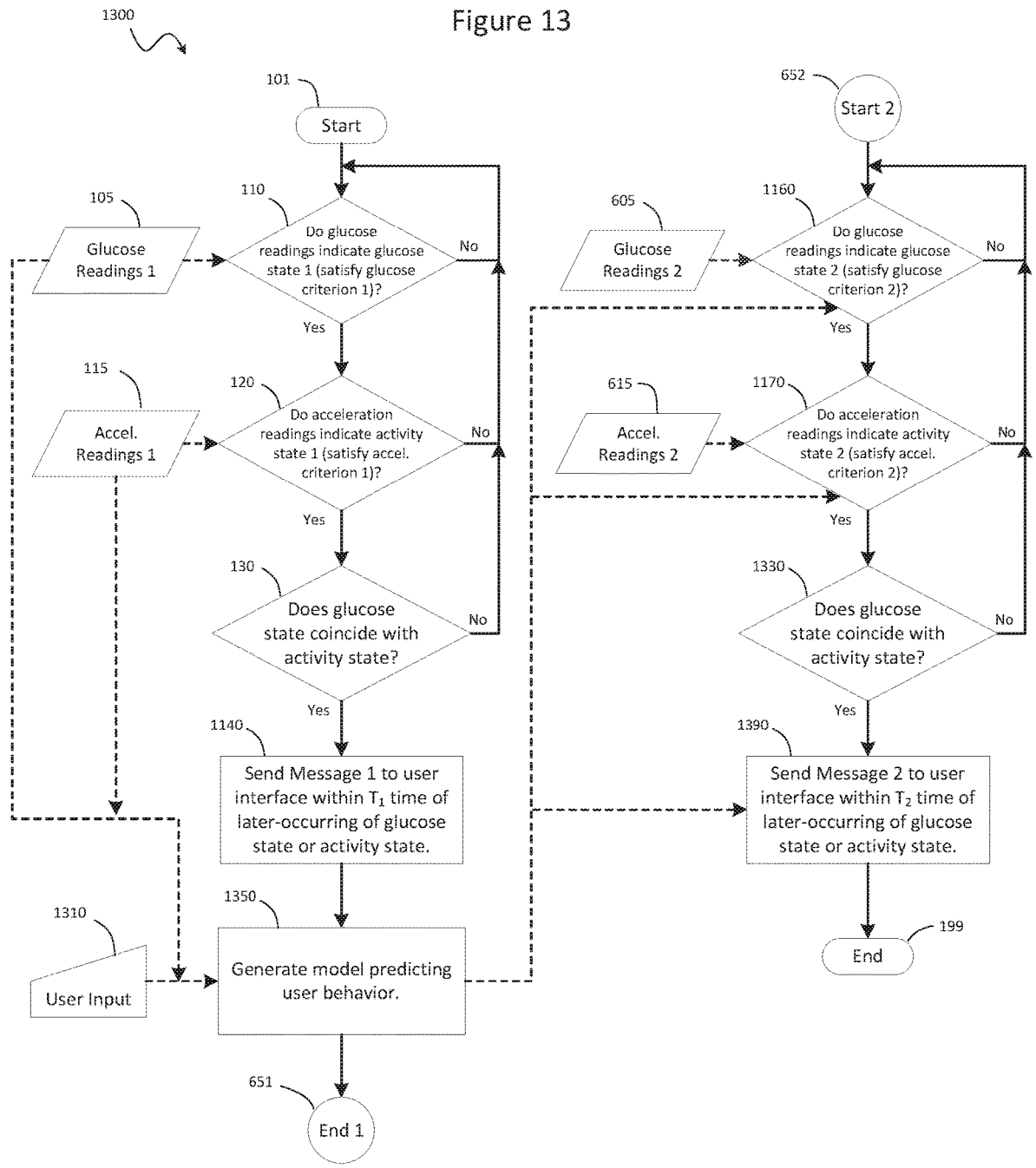
FIG. 13 presents a flowchart illustrating a method of regulating glucose levels using sensed data from a glucose monitor and an accelerometer and user inputs from a user interface in which a processing unit generates a model describing a relationship between glucose level and user activity according to certain embodiments of the present disclosure.

FIG. 13 presents a flowchart illustrating a method of regulating glucose levels using sensed data from a glucose monitor and an accelerometer and user inputs from a user interface in which a processing unit generates a model predicting a user behavior using glucose readings, according to certain embodiments of the present disclosure. After the start of a first time period (101), a processing unit determines whether a first set of glucose readings (105) satisfies a first set of glucose criteria, thereby indicating that the user is in a first glucose state. (110) If not, processing repeats step 110 until the processing unit detects the first glucose state. If the first glucose state is detected, the processing unit then determines whether a first set of acceleration readings (115) satisfies a first set of acceleration criteria, thereby indicating that the user is in a first activity state. (120) If not, processing returns to step 110 to determine whether glucose readings indicate the first glucose state. If the first activity state is detected, the processing unit then determines whether the first activity state coincides with (occurs at the same time as) the first glucose state. (130) If not, processing returns to step 110 until the first glucose state is detected. If the first glucose state and the first activity state coincide, the processing unit sends a message to a user interface within a first critical amount of time ($T_1$) after the first time at which the first glucose state and first activity state first coincide. (1140) The message recommends performing or abstaining from an activity that affects the user's glucose level. Using the first set of glucose readings (105), the first set of acceleration readings (115), and user inputs reporting eating activity (1310), the processing unit generates a model predicting user behavior. (1350) The first time period ends at 651.

After the start (652) of a second time period for FIG. 13, a processing unit determines whether a second set of glucose readings (605) satisfies a second set of glucose criteria, thereby indicating that the user is in a second glucose state. (1160) The second set of glucose criteria may be selected using the model generated at step 1350 and the glucose state may be indicative of the user behavior. If the second glucose state is not detected, the processing unit repeats step 1160 until it detects the second glucose state. If the second glucose state is detected, the processing unit then determines whether a second set of acceleration readings (615) satisfies a second set of acceleration criteria, thereby indicating that the user is in a second activity state. (1170) The second set of acceleration criteria may be chosen using the model generated at step 1350 and may be indicative of the user behavior. If the second activity state is not detected, processing returns to step 1160 to determine whether glucose readings indicate the second glucose state. If the second activity state is detected, the processing unit then determines whether the second activity state coincides with the second glucose state. (1330) If not, processing returns to step 1160 until the second glucose state is detected. If the second glucose state and the second activity state coincide, the processing unit sends a message to the user interface within a second critical amount of time ($T_2$) after the first time at which the second glucose state and second activity state first coincide. (1390) The second message may recommend performing or abstaining from the user behavior. $T_2$ may be selected using the model generated at step 1350. After the processing unit sends the second message to the user interface (1390), the method (1300) ends. (199)

System Embodiments

System embodiments may include a glucose monitor and an accelerometer communicatively coupled with a processing unit. The processing unit may be communicatively coupled with a user interface. System components may be housed in a single device or be distributed among multiple devices. Communicative coupling does not necessarily require a physical connection and indicates only that one system component may send information to or receive information from another component. If one component is communicatively coupled to another, it may be referred to as being in communication with the other component. One component may be in communication with another if, for example, it sends or receives electromagnetic transmissions to or from the other component.

A glucose monitor may refer to any device or component that measures glucose levels. The output of the monitor may be analog, digital, or of another format and may or may not require other devices or components to convert the output of the glucose monitor into a glucose level. Glucose monitors may include, for example, those in direct contact with blood or other bodily fluids or tissues or those measuring glucose without direct contact such as, for example, transmission and reflection spectroscopy. Continuous glucose monitoring (CGM) includes a variety of devices and techniques that measure glucose more frequently and automatically than was practical with earlier methods. In the context of CGM, continuous does not require that readings are either instantaneous or absolutely continuous. For example, CGM devices may provide measurements every five to ten minutes.

An accelerometer may refer to any device that measures either linear or angular acceleration. However, accelerometers measuring angular acceleration may also be referred to as gyroscopes, gyrometers, or simply gyros. An accelerometer may also refer to a device that measures acceleration in more than one direction and/or that measures both linear and angular acceleration. Devices referred to as nine-axis accelerometers measure both linear and angular acceleration along or around (respectively) three orthogonal axes as well as orientation of the accelerometer relative to magnetic fields such as that of the Earth. The axes of accelerometers with multiple axes may be orthogonal or approximately orthogonal. Acceleration readings may be used to estimate derived quantities of physical activity such as step count, calories burned, or distance traveled.

Measurements of glucose and acceleration may be expressed as electrical outputs from the glucose sensor and accelerometer, respectively. A reading may refer to the unprocessed output from a sensor or measurements derived from such outputs. Readings may include positive values, zero values or, where applicable, negative values. The glucose monitor and accelerometer may be communicatively coupled to a processing unit configured, through design or programming, to process outputs from the respective sensor types. Processing units may include one or more processors and any memory or other data storage necessary to process and store data. A processing unit may store instructions executed by its one or more processors. Instructions may allow the processor to identify a glucose state using the glucose readings, identify an activity state using acceleration readings, and determine whether the glucose state and the activity state coincide. The processing unit may, optionally, use user inputs regarding the user's activities to generate a model predicting the activities, the model generating predictions using the glucose readings from the glucose sensor and/or the acceleration readings from the accelerometer. The processing unit may, optionally, alter the one or more of the glucose criteria or the acceleration criteria or future messages based on the user input information.

The processing unit may be communicatively coupled to a user interface for presenting the message to a user. The user interface may present the message through one or more senses including visual, audio, or tactile outputs. Embodiments of the user interface may include, for example, a display screen, an audio speaker, or a tactile output. User interfaces may, optionally, include means for receiving user inputs including, for example, touch screens, key pads, microphones, or cameras.

Figure 14:
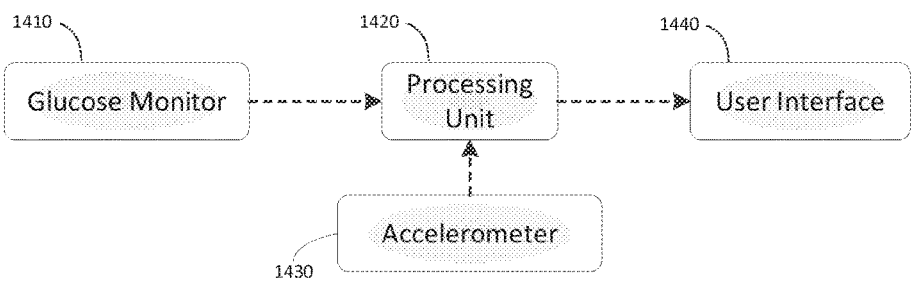
FIG. 14 presents a schematic diagram depicting an embodiment of a system comprising a glucose monitor, an accelerometer, a user interface, and a processing unit, according to certain embodiments of the present disclosure.

FIG. 14 presents a schematic diagram of a system (1400) according to certain embodiments of the present disclosure. The system (1400) includes a glucose monitor (1410) that is communicatively coupled to a processing unit (1420). The dashed line connecting the two components indicates that they are communicatively coupled; information may be transferred from one to another, but does not necessarily require a physical connection. An accelerometer (1430) may also be communicatively coupled to the processing unit (1420). The glucose monitor (1410) generates glucose readings that are indicative of glucose levels of a user. The processing unit (1420) is configured to determine whether the glucose readings satisfy one or more glucose criteria, thereby indicating that the user is in a specified glucose state. The accelerometer (1430) may be coupled to the user and generates acceleration readings indicative of the user's activity. The processing unit (1420) may be configured to determine whether the acceleration readings satisfy one or more acceleration criteria, thereby indicating that the user is in a specified activity state. If the processing unit (1420) determines that the user is in the glucose state and in the activity state and that the glucose state and activity state coincide (occur at the same time), the processing unit (1420) sends a message to the user interface (1440). The message may recommend performing or refraining from an activity that influences the user's glucose level.

Some embodiments locate the glucose sensor and the accelerometer within a single housing. The processing unit may also be located in the same housing. Alternatively, the glucose readings and acceleration readings may be communicated to an external processing unit. Communication may be through a wire or electromagnetic transmission. Similarly, the user interface may be located on the housing or on an external device.

Figure 15:
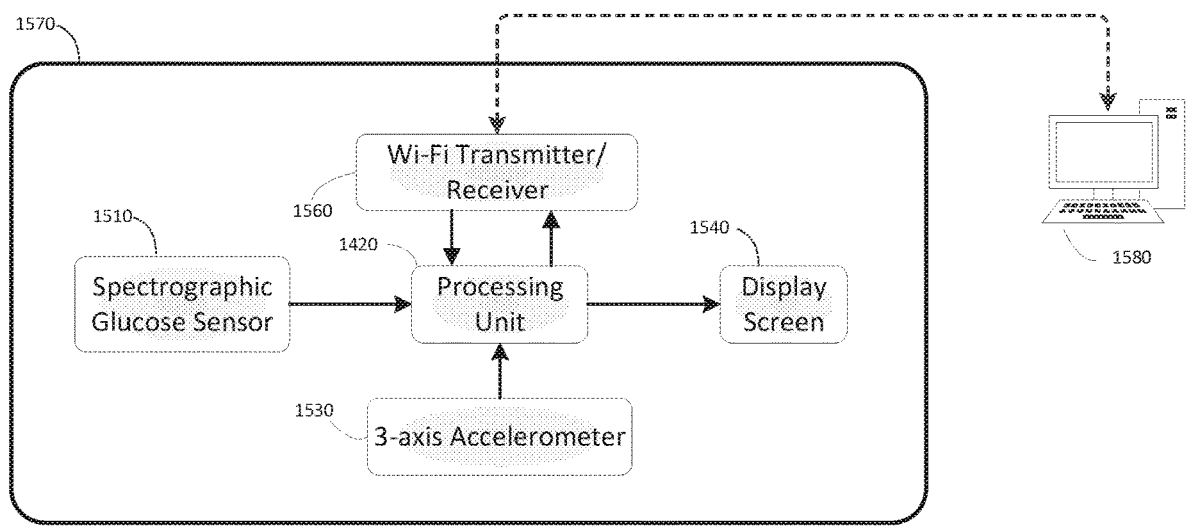
FIG. 15 presents a schematic diagram depicting an embodiment of a system comprising a glucose sensor, 3-axis accelerometer, display screen, and transmitter in a single device, according to certain embodiments of the present disclosure.

FIG. 15 presents a schematic diagram of a system (1500) housed in a single device, according to certain embodiments of the present disclosure. The rectangular perimeter (1570) surrounding the components indicates that the components are all located in the same device housing. The system (1500) comprises a spectrographic glucose monitor (1510), a processing unit (1420), a triaxial accelerometer (1530), and a display screen (1540) visible from the outside of the housing (1570). The processing unit (1420) may be configured to execute instructions for determining whether the glucose readings from the glucose sensor (1510) satisfy one or more glucose criteria, thereby indicating that a user of the system (1500) is in a glucose state. The processing unit (1420) may further be configured to execute instructions for determining whether the acceleration readings from the accelerometer (1520) satisfy one or more acceleration criteria, thereby indicating that a user of the system (1500) is in an activity state. If the processing unit (1420) determines that the user is in the glucose state and in the activity state and that the glucose state and the activity state coincide (occur at the same time), the processing unit (1420) sends a message to the display screen (1540) that displays the message. The message may recommend performing or refraining from an activity that influences glucose levels of the user. The display (1540) may perform other functions including, for example, informing the user of current blood glucose levels or activity level. From time to time, the system (1500) may communicate with a second device (1580) using radio signals. The system (1500) includes a Wi-Fi transmitter-receiver (1560) to exchange data with the external device (1580). The wireless communication may serve to communicate unprocessed or derived measures of glucose or motion to the external device (1580) which may be communicatively coupled to networks such as the Internet. Data regarding the messages presented and the glucose and motion conditions under which the messages were presented may also be communicated. Additionally, the wireless communication may be used to transfer updated instructions to the system (1500) from the second device (1580).

Smartphones are commonly carried by individuals and typically possess accelerometers, two-way user interfaces in the form of touch-screens, and processing units. Some embodiments combine the accelerometer, user interface, and processing unit of a smartphone with a glucose sensor housed separately. The glucose sensor may communicate glucose readings to the processing unit in the smartphone through electromagnetic signals using protocols such as Bluetooth or Wi-Fi. The touchscreen of the smartphone may serve not only to present messages to the user, but receive user inputs and send them to the processing unit. User inputs may include, for example, information regarding user activities such as the timing, content, and quantity of foods or medications consumed or physical activity performed. The touch-screen may display prompts (for example questions or surveys) that elicit user inputs to be entered on the touch-screen.

Figure 16:
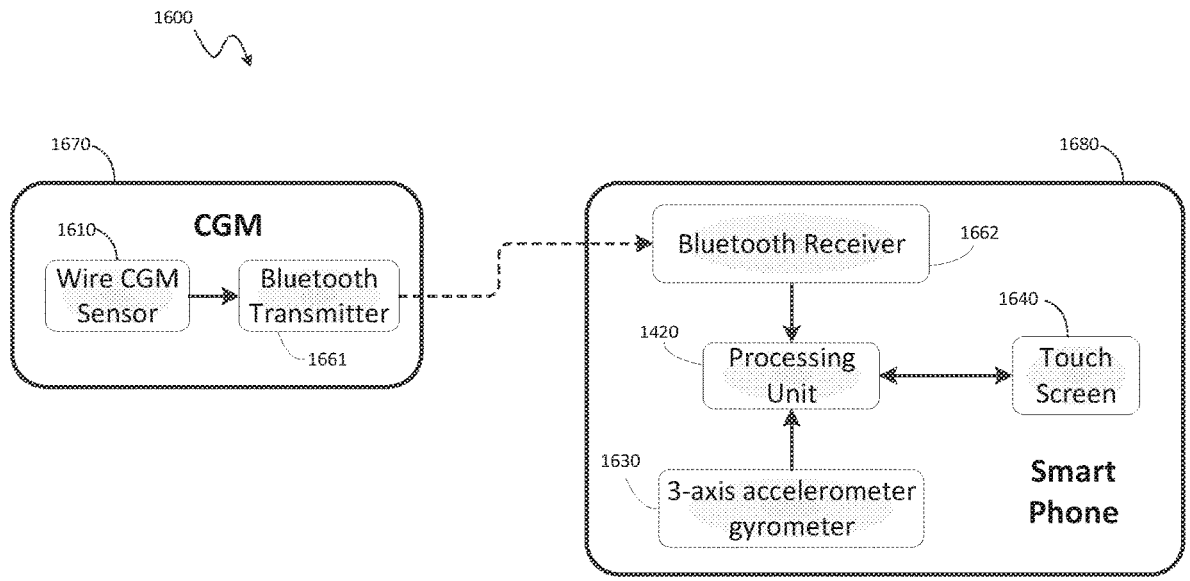
FIG. 16 presents a schematic diagram depicting an embodiment of a system comprising a CGM monitor and a smartphone comprising an accelerometer and touch-screen, according to certain embodiments of the present disclosure.

FIG. 16 presents a schematic diagram of a system (1600) in which components are housed in two separate devices, according to certain embodiments of the present disclosure. In this embodiment, one device is a CGM monitor (1670) and a second device is a smartphone (1680). The CGM monitor (1670) comprises a wire-based glucose sensor (1610) and a Bluetooth transmitter (1661). The Bluetooth transmitter (1661) may transmit glucose readings to a Bluetooth receiver (1662) located in the smartphone (1680). The Bluetooth receiver (1662) may then relay the glucose readings to the processing unit (1420). The processing unit (1420) also receives acceleration readings from an accelerometer (1630) located in the smartphone (1680). In this embodiment, the accelerometer (1630) is a three-axis accelerometer-gyrometer. The processing unit (1420) may be configured to execute instructions for determining whether the glucose readings from the CGM (1670) satisfy one or more glucose criteria, thereby indicating that a user of the system (1600) is in a glucose state. The processing unit (1420) may be further configured to execute instructions for determining whether the acceleration readings from the accelerometer (1620) satisfy one or more acceleration criteria, thereby indicating that a user of the system (1600) is in an activity state. If the processing unit (1420) determines that the user is in the glucose state and in the activity state and that the glucose state and the activity state coincide (occur at the same time), the processing unit (1420) may send a message to the touch-screen (1640) that displays the message. The message may recommend performing or refraining from an activity that influences glucose levels of the user. In addition to displaying the message, the touch-screen (1640) may perform other functions including, for example, sending user input information from the touch-screen (1640) to the processing unit (1420). The smartphone (1680) may, optionally, communicate raw or processed glucose and/or acceleration data to other external devices via cellular frequencies and data protocols.

While smartphones commonly comprise accelerometers capable of detecting activity, many users do not carry their smartphones on their person continuously, limiting the smartphone's utility for measuring user activity. An activity trackers is a small, lightweight device comprising an accelerometer. Activity trackers are typically worn on a wristband or on a belt-clip, but may be affixed anywhere on the body. Activity trackers are commonly worn throughout the day and sometimes while asleep. Activity trackers usually comprise means of uploading activity data to another device, for example a wired bus connector or radio transmitter. Some system embodiments comprise three separately-housed devices: an activity tracker, a glucose monitor, and a third device comprising a processing unit and user interface.

Figure 17:
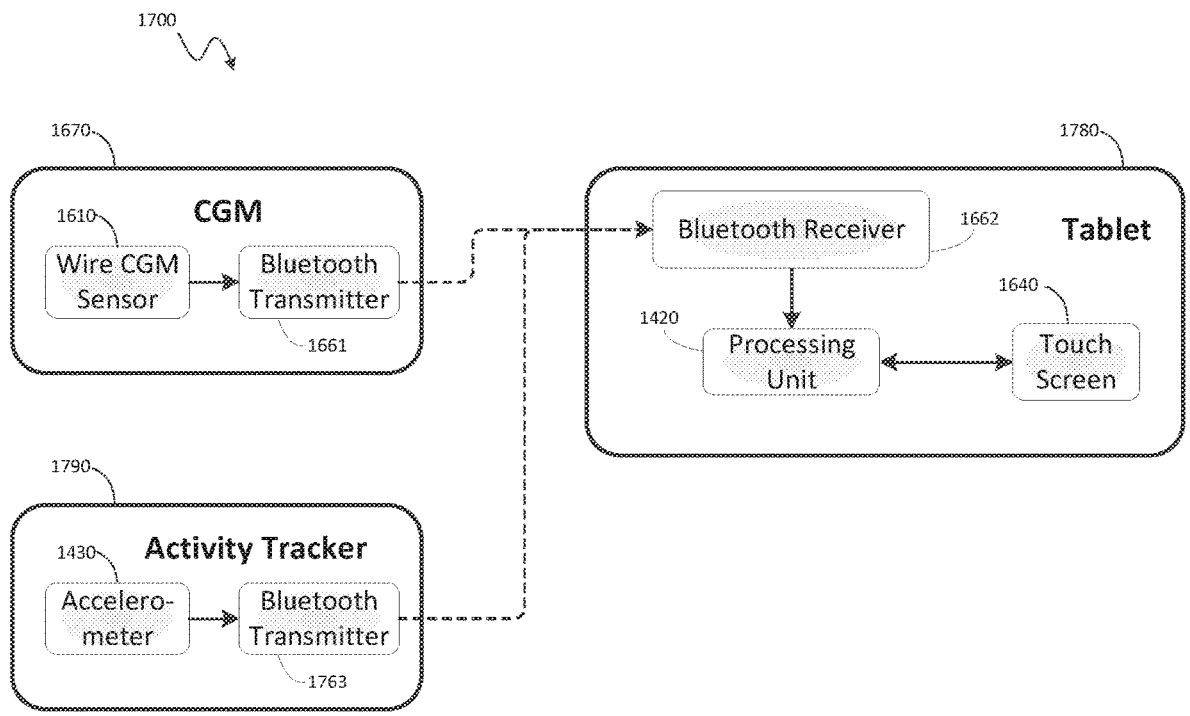
FIG. 17 presents a schematic diagram depicting an embodiment of a system comprising a CGM monitor, an activity tracker, and a tablet comprising a processing unit and a touch-screen, according to certain embodiments of the present disclosure.

FIG. 17 presents a schematic diagram of a system (1700) in which components are housed in three separate devices, according to certain embodiments of the present disclosure. One of the three devices is a CGM monitor (1670), a second is a tablet-style computing device (1780) and a third device is an activity tracker (1790). The CGM monitor (1670) comprises a wire-based glucose sensor (1610) and a Bluetooth transmitter (1661). The Bluetooth transmitter (1661) may transmit glucose readings to a Bluetooth receiver (1662) located in the tablet (1780). The Bluetooth receiver (1662) may then relay the glucose readings to a processing unit (1420). The activity tracker (1790) comprises an accelerometer (1430) and a second Bluetooth transmitter (1763). The Bluetooth transmitter (1763) may transmit acceleration readings to the Bluetooth receiver (1662) located in the tablet (1780). The Bluetooth receiver (1662) may then relay the glucose readings to the processing unit (1420). The processing unit (1420) may be configured to execute instructions for determining whether the glucose readings from the CGM (1670) satisfy one or more glucose criteria, thereby indicating that a user of the system (1700) is in a glucose state. The processing unit (1420) may further be configured to execute instructions for determining whether acceleration readings from the activity tracker (1790) satisfy one or more acceleration criteria, thereby indicating that the user is in an activity state. If the processing unit (1420) determines that the user is in the glucose state and in the activity state and that the glucose state and the activity state coincide (occur at the same time), the processing unit (1420) may send a message to the touch-screen (1640) that displays the message. The message may recommend performing or refraining from an activity that influences glucose levels of the user. In addition to displaying the message, the touch-screen (1640) may perform other functions including, for example, sending user input information from the touch-screen (1640) to the processing unit (1420). The touch-screen (1640) may display prompts (for example questions or surveys) that elicit user inputs to be entered on the touch-screen (1640). User inputs may include, for example, information regarding user activities such as the timing, content, and quantity of foods or medications consumed or physical activity performed. The processing unit (1420) may use user inputs regarding user activities to generate a model predicting the activities, the model generating predictions using the glucose readings from the CGM (1670) and/or the acceleration readings from the accelerometer (1630). The processing unit (1420) may alter one or more of the glucose criteria or the acceleration criteria or future messages based on the user input information.

Systems may comprise means of detecting other measures in addition to glucose level and acceleration. For example, embodiments may include a heart rate monitor, temperature sensor, or sensor measuring electrical activity or conductance on the skin. As with glucose monitors and accelerometers, readings from heart rate monitors may refer to the unprocessed outputs from a sensor or measurements derived from such outputs. The heart rate monitor may be communicatively coupled to a processing unit. Heart rate may be used to better understand glucose and acceleration readings and therefore be used to modify the one or more criteria or the message. For example, increasing glucose levels may be caused by eating but may also be caused by stress. If a heart rate monitor shows a fast heart rate when glucose levels are elevated and acceleration readings indicate little physical activity, the message may be altered from one regarding eating behavior to one regarding stress reduction.

Heart rate monitors may refer to any device or component that measures heart rate. Heart rate monitors measure heart rate using a variety of techniques including electro-cardiography (ECG) and photoplethysmography (PPG). ECG sensors may measure electrical potential on or near the surface of the skin using electrodes or other conductive material. PPG sensors measure changes in absorption of infrared light. These changes may be caused by variations in blood flow due to contractions of the heart. Derived metrics such as average heart rate and heart rate variability (HRV) may be calculated over various time periods. The data signal generated by PPG sensors may also be used for purposes other than estimating heart rate.

The above description is neither exclusive nor exhaustive and does not necessarily describe all possible embodiments (also called "examples"). The above description is not intended to limit the scope of the claims. Embodiments may include elements in addition to those described and, in some cases, may contain only a subset of the elements described in a particular embodiment. Embodiments may contain any combination of elements in the described embodiments in addition to elements not expressly described. As used herein, the articles "a" and "an" may include one or more than one of the noun modified by either without respect to other uses of phrases such as "one or more" or "at least one." The word "or" is used inclusively unless specified otherwise. Terms such as "first," "second," "third" and so forth are used as labels to distinguish elements and may not indicate sequential order unless otherwise indicated. In addition to the embodiments described above, embodiments may include any that would fall within the scope of the claims, below.

What is claimed is:

1. A method for generating and providing a superior message, the method comprising:
    during a first time period:
        receiving, by a processor, a first plurality of glucose readings indicative of first glucose levels of a user and a first plurality of acceleration readings indicative of first activity levels of the user, wherein (a) the first plurality of glucose readings is captured by a glucose monitor of the user, and (b) the first plurality of acceleration readings is captured by an accelerometer measuring acceleration of the user;
        identifying, by the processor, a first instance of a first glucose state, the first instance of the first glucose state occurring when the first plurality of glucose readings satisfies first glucose criteria;
        identifying, by the processor, a first instance of a first activity state, the first instance of the first activity state occurring when the first plurality of acceleration readings satisfies first acceleration criteria;
        determining, by the processor, that the first instance of the first glucose state coincides with the first instance of the first activity state;
        in response to determining that the first instance of the first glucose state coincides with the first instance of the first activity state, generating and providing, by the processor, a first message, wherein the first message (a) is generated and provided within a first configurable time period associated with the first glucose state or the first activity state, (b) is provided at a display, and (c) recommends a first behavior influencing the user's glucose levels;
        after generating and providing the first message, receiving, by the processor, a first plurality of post-message glucose readings indicative of glucose levels of the user, wherein the first plurality of post-message glucose readings is captured during a first post-message time period after providing the first message;
        determining, by the processor and using the first plurality of post-message glucose readings, a first post-message glucose change;
    during a second time period that is subsequent to the first time period:
        receiving, by the processor, a second plurality of glucose readings indicative of second glucose levels of the user and a second plurality of acceleration readings indicative of second activity levels of the user, wherein (a) the second plurality of glucose readings is captured by the glucose monitor of the user, and (b) the second plurality of acceleration readings is captured by the accelerometer measuring acceleration of the user;
        identifying, by the processor, a second instance of the first glucose state, the second instance of the first glucose state occurring when the second plurality of glucose readings satisfies the first glucose criteria;
        identifying, by the processor, a second instance of the first activity state, the second instance of the first activity state occurring when the second plurality of acceleration readings satisfies the first acceleration criteria;
        determining that the second instance of the first glucose state coincides with the second instance of the first activity state;
        in response to determining that the second instance of the first glucose state coincides with the second instance of the first activity state, generating and providing, by the processor, a second message, wherein the second message (a) is generated and provided within a second configurable time period associated with the first glucose state or the first activity state, (b) is provided at the display, and (c) recommends a second behavior influencing the user's glucose levels;
        after generating and providing the second message, receiving, by the processor, a second plurality of post-message glucose readings indicative of glucose levels of the user, wherein the second plurality of post-message glucose readings is captured during a second post-message time period after providing the second message; and
        determining, by the processor and using the second plurality of post-message glucose readings, a second post-message glucose change;
    during a third time period that is subsequent to the second time period:
        receiving, by the processor, a third plurality of glucose readings indicative of third glucose levels of the user and a third plurality of acceleration readings indicative of third activity levels of the user, wherein (a) the third plurality of glucose readings is captured by the glucose monitor of the user, and (b) the third plurality of acceleration readings is captured by the accelerometer measuring acceleration of the user;

identifying, by the processor, a third instance of the first glucose state, the third instance of the first glucose state occurring when the third plurality of glucose readings satisfies the first glucose criteria;

identifying, by the processor, a third instance of the first activity state, the third instance of the first activity state occurring when the third plurality of acceleration readings satisfies the first acceleration criteria;

determining, by the processor, that the third instance of the first glucose state coincides with the third instance of the first activity state;

selecting, by the processor, the first message or the second message as a superior message, wherein selecting the first message or the second message as the superior message is based on a comparison of the first post-message glucose change and the second post-message glucose change; and in response to determining that the third instance of the first glucose state coincides with the third instance of the first activity state, generating and providing, by the processor, the superior message, wherein the superior message is provided at the display during a fourth period of time:
generating, by the processor, a model predicting user behavior; and during a fifth period of time:
identifying, by the processor, a first instance of a second glucose state, the first instance of the second glucose state occurring when a fourth plurality of glucose readings satisfies second glucose criteria, the second glucose criteria selected using the model;

identifying, by the processor, a first instance of a second activity state, the first instance of the second activity state occurring when a fourth plurality of acceleration readings satisfies second acceleration criteria, the second acceleration criteria selected using the model;

determining, by the processor, that the first instance of the second glucose state coincides with the first instance of the second activity state; and in response to determining that the first instance of the second glucose state coincides with the first instance of the second activity state, generating and providing, by the processor, a third message, wherein the third message (a) is provided at the display and (b) recommends performing or abstaining from a third behavior.

2. The method of claim 1, wherein the first message comprises a recommendation with respect to one or more of: physical activity of the user, nutritional intake of the user, medication usage of the user, sleep of the user, or stress management techniques of the user.

3. A system comprising a processor and a memory, the processor configured to:

during a first time period:
receive a first plurality of glucose readings indicative of first glucose levels of a user and a first plurality of acceleration readings indicative of first activity levels of the user, wherein (a) the first plurality of glucose readings is captured by a glucose monitor of the user, and (b) the first plurality of acceleration readings is captured by an accelerometer measuring acceleration of the user;

identify a first instance of a first glucose state, the first instance of the first glucose state occurring when the first plurality of glucose readings satisfies first glucose criteria;

identify a first instance of a first activity state, the first instance of the first activity state occurring when the first plurality of acceleration readings satisfies first acceleration criteria;

determine that the first instance of the first glucose state coincides with the first instance of the first activity state;

in response to determining that the first instance of the first glucose state coincides with the first instance of the first activity state, generate and provide a first message, wherein the first message (a) is generated and provided within a first configurable time period associated with the first glucose state or the first activity state, (b) is provided at a display, and (c) recommends a first behavior influencing the user's glucose levels;

after generating and providing the first message, receive a first plurality of post-message glucose readings indicative of glucose levels of the user, wherein the first plurality of post-message glucose readings is captured during a first post-message time period after providing the first message; and determine, using the first plurality of post-message glucose readings, a first post-message glucose change;

during a second time period that is subsequent to the first time period:
receive a second plurality of glucose readings indicative of second glucose levels of the user and a second plurality of acceleration readings indicative of second activity levels of the user, wherein (a) the second plurality of glucose readings is captured by the glucose monitor of the user, and (b) the second plurality of acceleration readings is captured by the accelerometer measuring acceleration of the user;

identify a second instance of the first glucose state, the second instance of the first glucose state occurring when the second plurality of glucose readings satisfies the first glucose criteria;

identify a second instance of the first activity state, the second instance of the first activity state occurring when the second plurality of acceleration readings satisfies the first acceleration criteria;

determine that the second instance of the first glucose state coincides with the second instance of the first activity state;

in response to determining that the second instance of the first glucose state coincides with the second instance of the first activity state, generate and provide a second message, wherein the second message (a) is generated and provided within a second configurable time period associated with the first glucose state or the first activity state, (b) is provided at the display, and (c) recommends a second behavior influencing the user's glucose levels;

after generating and providing the second message, receive a second plurality of post-message glucose readings indicative of glucose levels of the user, wherein the second plurality of post-message glucose readings is captured during a second post-message time period after providing the second message; and determine, using the second plurality of post-message glucose readings, a second post-message glucose change;

during a third time period that is subsequent to the second time period:
receive a third plurality of glucose readings indicative of third glucose levels of the user and a third plurality of acceleration readings indicative of third activity levels of the user, wherein (a) the third plurality of glucose readings is captured by the glucose monitor of the user, and (b) the third plurality of acceleration readings is captured by the accelerometer measuring acceleration of the user;
identify a third instance of the first glucose state, the third instance of the first glucose state occurring when the third plurality of glucose readings satisfies the first glucose criteria;
identify a third instance of the first activity state, the third instance of the first activity state occurring when the third plurality of acceleration readings satisfies the first acceleration criteria;
determine that the third instance of the first glucose state coincides with the third instance of the first activity state;
select the first message or the second message as a superior message, wherein selecting the first message or the second message as the superior message is based on a comparison of the first post-message glucose change and the second post-message glucose change; and
in response to determining that the third instance of the first glucose state coincides with the third instance of the first activity state, generate and provide the superior message, wherein the superior message is provided at the display during a fourth period of time:
generate a model predicting user behavior; and during a fifth period of time:
identify a first instance of a second glucose state, the first instance of the second glucose state occurring when a fourth plurality of glucose readings satisfies second glucose criteria, the second glucose criteria selected using the model;
identify a first instance of a second activity state, the first instance of the second activity state occurring when a fourth plurality of acceleration readings satisfies second acceleration criteria, the second acceleration criteria selected using the model;
determine that the first instance of the second glucose state coincides with the first instance of the second activity state; and
in response to determining that the first instance of the second glucose state coincides with the first instance of the second activity state, generate and provide a third message, wherein the third message (a) is provided at the display and (b) recommends performing or abstaining from a third behavior.

4. The system of claim 3, wherein the first message comprises a recommendation with respect to one or more of: physical activity of the user, nutritional intake of the user, medication usage of the user, sleep of the user, or stress management techniques of the user.

* * * * *